US010390991B2

(12) United States Patent
Rogers et al.

(10) Patent No.: US 10,390,991 B2
(45) Date of Patent: Aug. 27, 2019

(54) MEDICAL DEVICES INCORPORATING THERMOELECTRIC TRANSDUCER AND CONTROLLER

(75) Inventors: Lesco L. Rogers, Raleigh, NC (US); Jesko von Windheim, Wake Forest, NC (US); Seri Lee, Honolulu, HI (US)

(73) Assignee: SCION NEUROSTIM, LLC, Raleigh, NC (US)

( * ) Notice: Subject to any disclaimer, the term of this patent is extended or adjusted under 35 U.S.C. 154(b) by 1074 days.

(21) Appl. No.: 13/584,853

(22) Filed: Aug. 14, 2012

(65) Prior Publication Data

US 2012/0310313 A1   Dec. 6, 2012

Related U.S. Application Data

(63) Continuation of application No. 12/693,016, filed on Jan. 25, 2010, now Pat. No. 8,267,983, which is a
(Continued)

(51) Int. Cl.
*A61F 7/00* (2006.01)
*F25B 21/02* (2006.01)
*H01L 35/32* (2006.01)

(52) U.S. Cl.
CPC ............. *A61F 7/007* (2013.01); *F25B 21/02* (2013.01); *H01L 35/32* (2013.01); *A61F 2007/0075* (2013.01); *F25B 2321/021* (2013.01)

(58) Field of Classification Search
CPC ... A61F 7/007; A61F 2007/0075; F25B 21/02
See application file for complete search history.

(56) References Cited

U.S. PATENT DOCUMENTS

| 4,117,881 A | 10/1978 | Williams et al. |
| 4,244,377 A | 1/1981 | Grams |

(Continued)

FOREIGN PATENT DOCUMENTS

| DE | 100 65 592 A1 | 7/2002 |
| JP | H08195997 | 7/1996 |

(Continued)

OTHER PUBLICATIONS

Brookler, "Simultaneous Bilateral Bithermal Caloric Stimulation in Electronystagmography," Presented at the Meeting of the Eastern Section of the American Laryngological Rhinological and Otological Society, Inc., Britannia Beach Hotel, Paradise Island, Nassau, Jan. 17, 1971.
(Continued)

*Primary Examiner* — Eun Hwa Kim
(74) *Attorney, Agent, or Firm* — Myers Bigel, P.A.

(57) ABSTRACT

A temperature control system may include a thermoelectric device, a controller electrically coupled to the thermoelectric device, a heat transfer structure thermally coupled to the thermoelectric device, a temperature controlled medium thermally coupled to the thermoelectric device and a temperature feedback sensor. The controller may be configured to sense a first value of an electrical characteristic of the thermoelectric device and to generate a first electrical control to activate the thermoelectric device in response to sensing the first value of the electrical characteristic of the thermoelectric device. The controller may be further configured to sense a second value of the electrical characteristic of the thermoelectric device and to generate a second electrical control signal to activate the thermoelectric device in response to sensing the second value of the electrical characteristic of the thermoelectric device.

55 Claims, 11 Drawing Sheets

Related U.S. Application Data continuation-in-part of application No. 12/166,953, filed on Jul. 2, 2008, now abandoned, which is a continuation-in-part of application No. 11/972,267, filed on Jan. 10, 2008, now abandoned.

(60) Provisional application No. 61/224,668, filed on Jul. 10, 2009, provisional application No. 60/884,546, filed on Jan. 11, 2007, provisional application No. 60/908,261, filed on Mar. 27, 2007.

(56) References Cited

U.S. PATENT DOCUMENTS

| | | |
|---|---|---|
| 4,449,528 A | 5/1984 | Auth et al. |
| 4,860,748 A | 8/1989 | Chiurco |
| 4,918,757 A | 4/1990 | Janssen et al. |
| 5,097,828 A | 3/1992 | Deutsch |
| 5,190,539 A | 3/1993 | Fletcher et al. |
| 5,215,086 A | 6/1993 | Terry, Jr. et al. |
| 5,367,890 A | 11/1994 | Doke |
| 5,376,184 A | 12/1994 | Aspden |
| 5,419,780 A | 5/1995 | Suski |
| 5,746,702 A | 5/1998 | Gelfgat et al. |
| 5,762,612 A | 6/1998 | Campbell |
| 5,837,929 A | 11/1998 | Adelman |
| 5,871,526 A | 2/1999 | Gibbs et al. |
| 6,016,449 A | 1/2000 | Fischell et al. |
| 6,017,337 A * | 1/2000 | Pira ............... A61B 18/02 |
| | | 601/15 |
| 6,055,815 A | 5/2000 | Peterson |
| 6,094,918 A | 8/2000 | Burbidge |
| 6,143,975 A | 11/2000 | Liao et al. |
| 6,165,173 A | 12/2000 | Kamdar et al. |
| 6,300,150 B1 | 10/2001 | Venkatasubramanian |
| 6,334,311 B1 | 1/2002 | Kim et al. |
| 6,511,437 B1 | 1/2003 | Nakamura et al. |
| 6,746,474 B2 | 6/2004 | Saadat |
| 6,755,026 B2 | 6/2004 | Wallach |
| 6,817,191 B2 | 11/2004 | Watanabe |
| 6,875,196 B2 | 4/2005 | Abita et al. |
| 6,882,881 B1 | 4/2005 | Lesser et al. |
| 6,909,917 B2 | 6/2005 | Woods et al. |
| 6,921,195 B2 | 7/2005 | Pipe et al. |
| 6,981,381 B1 | 1/2006 | Wang et al. |
| 7,082,772 B2 | 8/2006 | Welch |
| 7,164,077 B2 | 1/2007 | Venkatasubramanian |
| 7,189,252 B2 | 3/2007 | Krueger |
| 7,234,735 B2 | 6/2007 | Harada |
| 7,761,168 B2 | 7/2010 | Gross |
| 7,856,275 B1 | 12/2010 | Paul et al. |
| 8,083,786 B2 | 12/2011 | Gafni et al. |
| 8,460,356 B2 | 6/2013 | Rogers et al. |
| 9,283,111 B2 | 3/2016 | Rogers et al. |
| 2002/0072781 A1 | 6/2002 | Lattner et al. |
| 2002/0104318 A1 | 8/2002 | Jaafar et al. |
| 2002/0121094 A1 | 9/2002 | VanHoudt |
| 2003/0097845 A1 * | 5/2003 | Saunders ............ A41D 13/005 |
| | | 62/3.3 |
| 2003/0099279 A1 | 5/2003 | Venkatasubramanian et al. |
| 2003/0101006 A1 | 5/2003 | Mansky et al. |
| 2003/0158589 A1 | 8/2003 | Katsnelson |
| 2003/0195588 A1 * | 10/2003 | Fischell ............... A61N 2/02 |
| | | 607/55 |
| 2004/0102525 A1 | 5/2004 | Kozachuk |
| 2004/0181269 A1 | 9/2004 | Lee |
| 2004/0193237 A1 | 9/2004 | Krueger |
| 2005/0107682 A1 | 5/2005 | Rao et al. |
| 2005/0145273 A1 | 7/2005 | Atwood et al. |
| 2005/0165460 A1 | 7/2005 | Erfan |
| 2005/0203505 A1 | 9/2005 | Megerman et al. |
| 2006/0082971 A1 | 4/2006 | Artman et al. |
| 2006/0086118 A1 | 4/2006 | Venkatasubramanian et al. |
| 2006/0095088 A1 | 5/2006 | De Ridder |
| 2006/0289050 A1 | 12/2006 | Alley et al. |
| 2006/0289052 A1 | 12/2006 | O'Quinn et al. |
| 2006/0293732 A1 | 12/2006 | Collins et al. |
| 2007/0028956 A1 | 2/2007 | Venkatasubramanian et al. |
| 2007/0083097 A1 | 4/2007 | Fujiwara et al. |
| 2007/0087780 A1 | 4/2007 | Nassimi |
| 2007/0089773 A1 | 4/2007 | Koester et al. |
| 2007/0135880 A1 | 6/2007 | Eggers et al. |
| 2007/0167985 A1 | 7/2007 | Kirby |
| 2007/0198063 A1 | 8/2007 | Hunter et al. |
| 2007/0203539 A1 | 8/2007 | Stone et al. |
| 2007/0215194 A1 | 9/2007 | Bharathan et al. |
| 2007/0225781 A1 | 9/2007 | Saadat et al. |
| 2007/0226890 A1 | 10/2007 | Pflueger |
| 2007/0250119 A1 | 10/2007 | Tyler et al. |
| 2007/0265524 A1 | 11/2007 | Eda et al. |
| 2008/0015667 A1 | 1/2008 | Gross |
| 2008/0087316 A1 | 4/2008 | Inaba et al. |
| 2008/0097549 A1 | 4/2008 | Colbaugh et al. |
| 2008/0154334 A1 | 6/2008 | Gavronsky |
| 2008/0168775 A1 | 7/2008 | Windheim et al. |
| 2008/0182399 A1 | 7/2008 | Cho |
| 2008/0264464 A1 | 10/2008 | Lee |
| 2009/0082831 A1 | 3/2009 | Paul et al. |
| 2009/0182399 A1 * | 7/2009 | Sylvestre ............ A61F 7/12 |
| | | 607/99 |
| 2010/0198204 A1 | 8/2010 | Rogers et al. |
| 2010/0198282 A1 | 8/2010 | Rogers |
| 2010/0198318 A1 | 8/2010 | Rogers |
| 2010/0211142 A1 | 8/2010 | Rogers et al. |
| 2011/0313498 A1 | 12/2011 | Smith et al. |
| 2011/0313499 A1 | 12/2011 | Smith et al. |
| 2012/0078337 A1 | 3/2012 | Darley et al. |
| 2012/0316624 A1 | 12/2012 | Smith et al. |

FOREIGN PATENT DOCUMENTS

| | | |
|---|---|---|
| JP | H09285468 | 11/1997 |
| JP | 2002-123456 A | 4/2002 |
| JP | 2006102258 | 4/2006 |
| JP | 2007-144057 A | 6/2007 |
| WO | WO 00/66215 A1 | 11/2000 |
| WO | WO 02/064069 A2 | 8/2002 |
| WO | WO 2005/074463 A2 | 8/2005 |
| WO | WO 2006/079484 A1 | 8/2006 |
| WO | WO 2007/051911 A1 | 5/2007 |
| WO | WO 2009/020862 A2 | 2/2009 |
| WO | WO 2010/029536 | 3/2010 |
| WO | WO 2012/083126 | 6/2012 |

OTHER PUBLICATIONS

Coats, "Temperature effects on the peripheral auditory apparatus" Science, Dec. 10, 1965; 150 (702): 1481-1483.
Ettenberg et al., "A New n-type and Improved p-type Pseudo-ternary (Bi2Te3)(Sb2Se3) Alloy for Peltier Cooling" 15th International Conference on Thermoelectrics, IEEE Catalog No. 96TH8169 pp. 52-56 (1996).
Examination Report, AU 2008284042, dated Oct. 9, 2012.
Fontanazza, "A Cooler Way to Stop Seizures" Medical Device & Diagnostic Industry Magazine pp. 1-2 (2005).
International Search Report and Written Opinion, PCT/US2008/071935, dated Jul. 16, 2009.
Kolev, "How caloric vestibular irritation influences migraine attacks" Cephalalgia 10:167-169, 1990.
Litchfield, "Biomedical Device Maker Teams with NASA to Develop Nano-Sized Biothermal Battery", http://www.devicelink.com/emdm/archive/04/10/002.html, 2 pages, European Medical Device Manufacturer (Oct. 2004).
Mast et al., "Visual mental imagery during caloric vestibular stimulation", Neuropsychologia 44(1):101-109 (2006).
Miller et al., "Studies of caloric vestibular stimulation: implications for the cognitive neurosciences, the clinical neurosciences and neurophilosophy", Acta Neuropsychiatrica 19:183-203 (2007).
Nextreme Thermal Solutions, Inc., "Breakthroughs: Thermoelectric Generator Converts Waste Heat into Energy" MPMN Oct. 2007 http:/www.devicelink.com/mpmn/archive/07/10/014.html.

(56) References Cited

OTHER PUBLICATIONS

Ried, "Asymmetries of Vestibular Dysfunction in Major Depression" Neuroscience 144:128-134, 2007.
Rode et al., "Bilateral vestibular stimulation does not improve visual hemineglect," Neuropsychologia 40:1104-1106 (2002).
Rothman, "Pathophysiology and therapy of epilepsy", 2 pages, Website of Professor Steven Rothman, M.D., Washington University of St. Louis: http://neuroscience.wus/edu/research/faculty.php?id=81.
Snyder et al., "Hot Spot Cooling using Embedded Thermoelectric Coolers", 22nd IEEE SEMI-THERM Symposium, IEEE Catalog No. 1-4244-0154-2, pp. 135-143 (2006).
Tellurex Corp., "Thermoelectric cooling semiconductor modules available in new configuration" MPMN: Cover Products Apr. 1999 http://www.devicelink.com/mpmn/archive/99/04/cover.html.
Venkatasubramanian et al., "Phonon-Blocking Electron-Transmitting Structures" 18th International Conference on Thermoelectrics (1999).
Japanese Patent Application No. 2010-519241; filed Jan. 28, 2010; office action dated Dec. 4, 2012.
U.S. Appl. No. 12/704,872; filed Feb. 12, 2010; Office Action dated Jan. 29, 2013.
Extended European Search Report Corresponding to European Application No. 14163419.6, dated Jan. 8, 2015; 3 Pages.
U.S. Appl. No. 13/525,817, filed Aug. 18, 2012; Office Action dated May 9, 2014.
Baier et al., "Evidence for Modulation of Opioidergic Activity in Central Vestibular Processing: A [$^{18}$F] Diprenorphine PET Study," Hum. Brain Mapp, 31:550-555 (2010).
Been et al., "The use of tDCS and CVS as methods of non-invasive brain stimulation," J. Brain Res. Rev. 56:346-361 (2007).
Bense et al., "Preserved visual-vestibular interaction in patients with bilateral vestibular failure," Neurol. 63:122-128 (2004).
Deutschländer et al., "Sensory System Interactions During Simultaneous Vestibular and Visual Stimulation in PET," Hum. Brain Mapp. 16:92-103 (2002).
Dieterich et al., "Functional brain imaging of peripheral and central vestibular disorders," Brain 131:2538-2552 (2008).
Fasold et al., "Human Vestibular Cortex as Identified with Caloric Stimulation in Functional Magnetic Resonance Imaging," NeuroImage 17:1384-1393 (2002).
Ferré et al., "Vestibular inputs modulate somatosensory cortical processing," Brain Struct. Funct. 217:859-864 (2012).
Ferré et al., "Vestibular modulation of somatosensory perception," Eur. J. Neurosci. 34:1337-1344 (2011).
International Preliminary Report on Patentability Corresponding to International Application No. PCT/US2011/065328; dated Jun. 27, 2013; 12 Pages.
International Preliminary Report on Patentability Corresponding to International Application No. PCT/US2011/065321; dated Jun. 27, 2013; 9 Pages.
International Preliminary Report on Patentability Corresponding to International Application No. PCT/US2011/065396; dated Jun. 27, 2013; 7 Pages.
International Preliminary Report on Patentability Corresponding to International Application No. PCT/US2011/065338; dated Jun. 27, 2013; 7 Pages.
International Preliminary Report on Patentability Corresponding to International Application No. PCT/US2011/065456; dated Jun. 27, 2013; 8 Pages.
International Preliminary Report on Patentability Corresponding to International Application No. PCT/US2010/060764, dated Jun. 28, 2012; 9 Pages.
International Preliminary Report on Patentability for Application No. PCT/US10/60771, dated May 17, 2012.
International Search Report and Written Opinion Corresponding to International Application No. PCT/US2011/065328; dated Mar. 29, 2012; 13 Pages.
International Search Report and Written Opinion Corresponding to International Application No. PCT/US2011/065321; dated Mar. 29, 2012; 10 Pages.
International Search Report and Written Opinion Corresponding to International Application No. PCT/US2011/065396; dated Apr. 23, 2012; 8 Pages.
International Search Report and Written Opinion Corresponding to International Application No. PCT/US2011/065338; dated Apr. 20, 2012; 8 Pages.
International Search Report and Written Opinion Corresponding to International Application No. PCT/US2011/065456; dated Apr. 4, 2012; 9 Pages.
International Search Report and Written Opinion Corresponding to International Application No. PCT/US2010/060764; dated Feb. 22, 2011.
International Search Report and Written Opinion for PCT/US2010/060771 dated Feb. 22, 2011.
Karim et al., "Neuroimaging to detect cortical projection of vestibular response to caloric stimulation in young and older adults using functional near-infrared spectroscopy (fNIRS)," NeuroImage 76:1-10 (2013).
Kimm et al., "Vestibular Effects of Electrical Stimulation of the Cochlea," Arch. Otolaryngol. 105:175-179 (1979).
Klingner et al., "Components of vestibular cortical function," Behav. Brain Res. 236:194-199 (2013).
Lobel et al., "Functional MRI of Galvanic Vestibular Stimulation," J. Neurophysiol. 80:2699-2709 (1998).
Lopez et al., "The Human Vestibular Cortex Revealed by Coordinate-Based Activation Likelihood Estimation Meta-Analysis," Neurosci. 212:159-179 (2012).
Marcelli et al., "Spatio-temporal pattern of vestibular information processing after brief caloric stimulation," Eur. J. of Radiol. 70:312-316 (2009).
Marcelli et al; "Spatio-temporal pattern of vestibular information processing after brief caloric stimulation"; (2008) EJR (European Journal of Radiology) Elsevier EURR-3758; Number of pp. 5.
McGeoch et al., "Post-stroke tactile allodynia and its modulation by vestibular stimulation: a MEG case study," Acta Neurol. Scand 119:404-409 (2009).
Naito et al., "Cortical correlates of vestibule-ocular reflex modulation: a PET study," Brain 126:1562-1578 (2003).
Ramachandran et al., "Can vestibular caloric stimulation be used to treat apotemnophilia?," Med. Hypotheses 69:250-252 (2007).
Schiff et al., "Does vestibular stimulation activate thalamocortical mechanisms that reintegrate impaired cortical regions?," Proc. R. Soc. Lond. 266:421-423 (1999).
Vitte et al., "Activation of the hippocampal formation by vestibular stimulation: a functional magnetic resonance imaging study," Exp. Brain Res. 112:523-526 (1996).
Zhang Na, et al; "Change of extracellular ascorbic acid in the brain cortex following ice water vestibular stimulation: an on-line electrochemical detection coupled with in vivo microdialysis sampling for guinea pigs"; Chin Med J. 2008: 121 (12): 1120-1125.
Shinji Nishizawa, "Intervals for Successive Caloric Irrigations", Equilibrium Research, Japan Society for Equilibrium Research, 2001, vol. 60, p. 86-92.

* cited by examiner

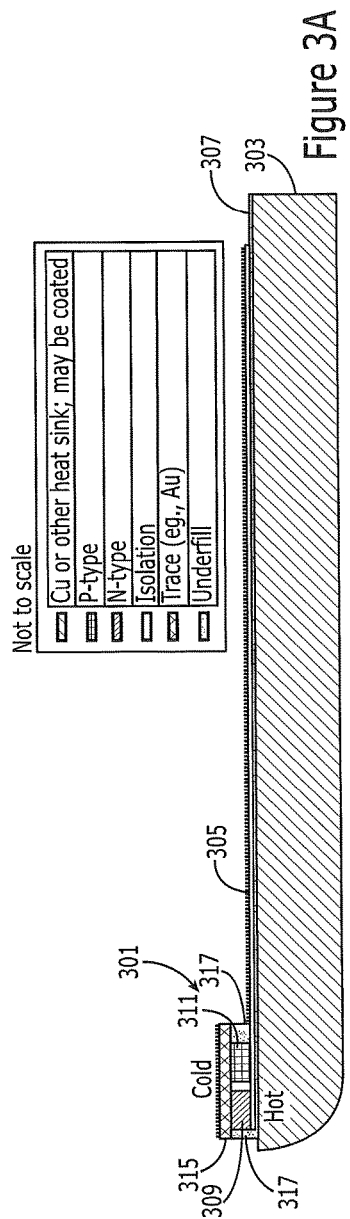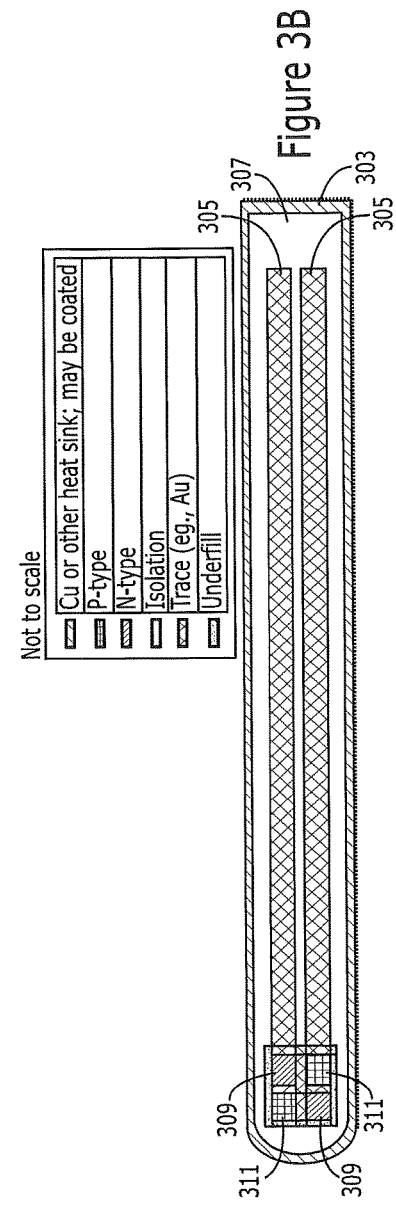

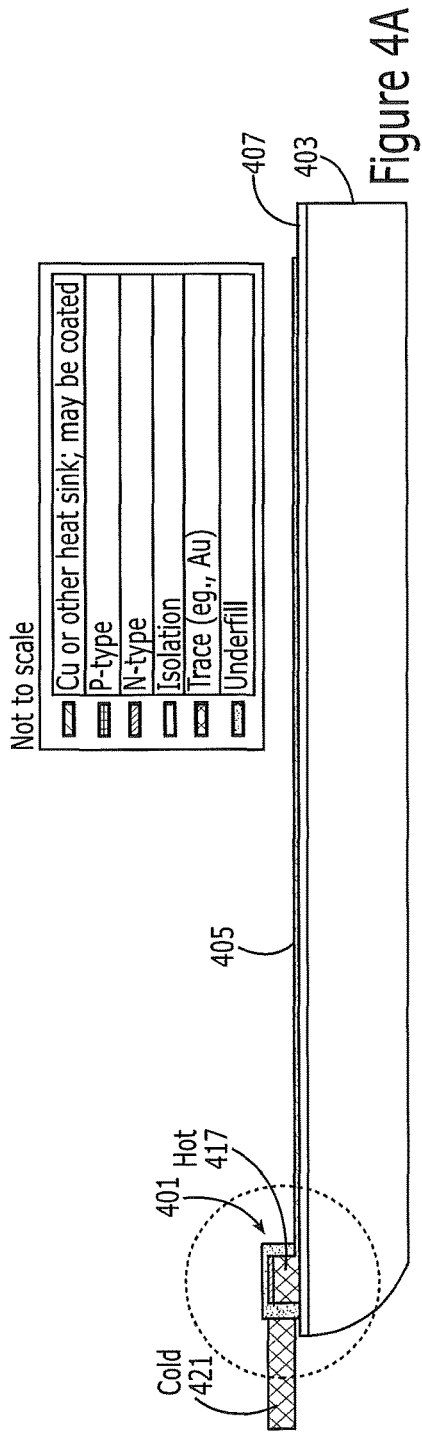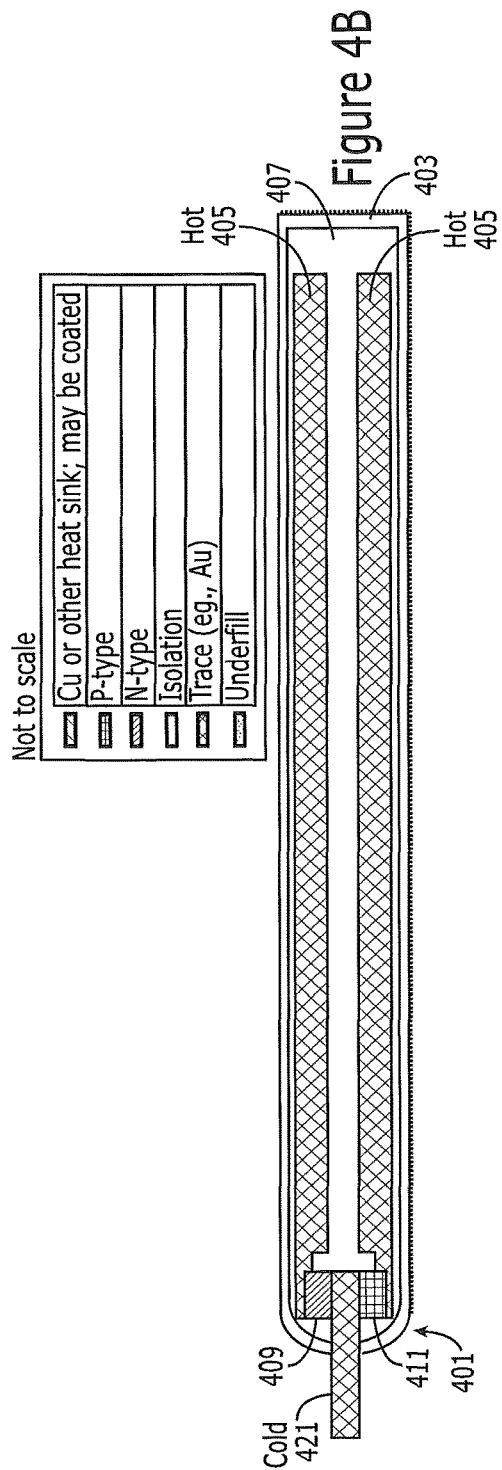

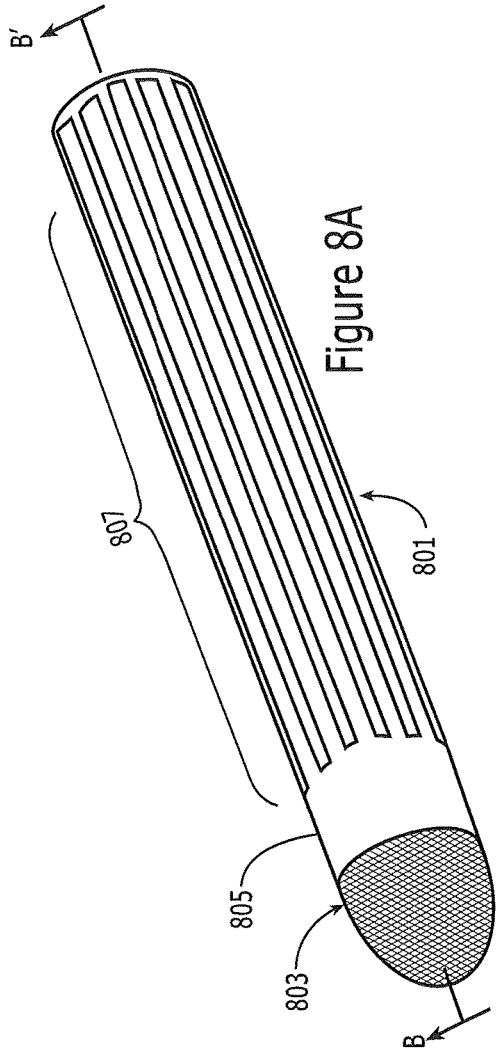
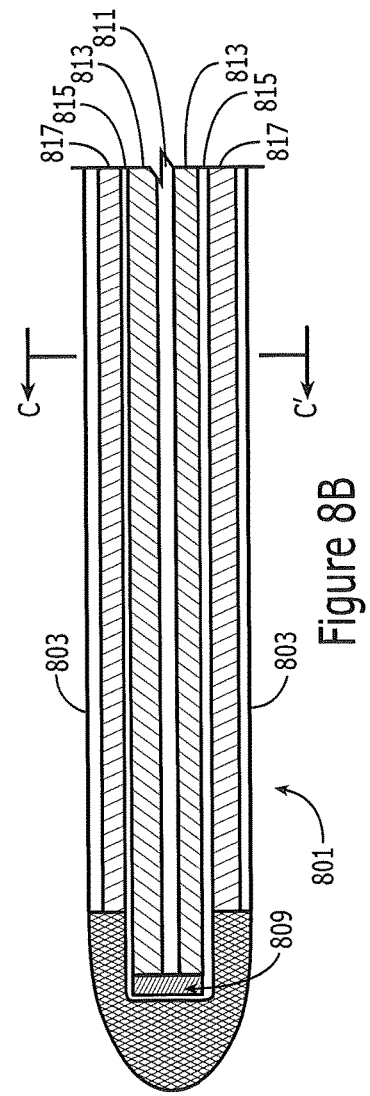

An expression for determining termperature response to heat injected/removed into/out from a body Uniform heat-flux input, $q''$ (W/m^2) Over the surface Note: for cooling, $q''$ can be either positive for heating or negative for cooling.

Semi-infinite substrate (i.e. body-part) with $\kappa, \alpha$

The temperature of the substrate as a function of depth, x and time, t, is given as:

$$T(x,t) - T_0 = \frac{2q''\sqrt{\alpha t/\pi}}{\kappa} \exp\left(\frac{-x^2}{4\alpha t}\right) - \frac{q''x}{\kappa} \text{erfc}\left(\frac{x}{2\sqrt{\alpha t}}\right)$$

where,
$T_0$ = initial body temperature (°C) at $t = 0$
$\alpha$ = thermal diffusivity (m^2/s) $\qquad a = \frac{\kappa}{\rho C_\rho}$ with $\rho$ = density (kg/m^3); $C_\rho$ = specific heat (J/kg-K)
$\kappa$ = thermal conductivity (W/mK)

$\text{erfc}(w) = 1 - \frac{2}{\sqrt{\pi}} \zeta \, e^{-z^2} dz$ :complementary error function which can be determined using the method of numerical integration, or using an approximate series expansion solution from a reference book on Special Functions

Figure 11

MEDICAL DEVICES INCORPORATING THERMOELECTRIC TRANSDUCER AND CONTROLLER

RELATED APPLICATIONS

This application claims priority under 35 U.S.C. § 120 to, and is a continuation of, Ser. No. 12/693,016, filed Jan. 25, 2010, now U.S. Pat. No. 8,267,983 which claims the benefit of priority under 35 U.S.C. § 119(e) to U.S. Provisional Application No. 61/224,668, filed Jul. 10, 2009 and which is itself a continuation-in-part of U.S. patent application Ser. No. 12/166,953, filed Jul. 2, 2008, now abandoned which is itself a continuation-in-part of U.S. patent application Ser. No. 11/972,267, filed Jan. 10, 2008, now abandoned which claims the benefit of priority under 35 U.S.C. § 119(e) to U.S. Provisional Application No. 60/884,546, filed Jan. 11, 2007, and to U.S. Provisional Application No. 60/908,261, filed Mar. 27, 2007, the disclosure of each of which is incorporated herein by reference in its entirety.

FIELD OF THE INVENTION

The present invention relates to medical instruments, and more particularly, to medical instruments incorporating a thermoelectric transducer and controller.

BACKGROUND

Thermoelectric materials may be used to provide cooling and/or power generation according to the Peltier effect. Thermoelectric materials are discussed, for example, in the reference by Venkatasubramanian et al. entitled "Phonon-Blocking Electron-Transmitting Structures" (18th International Conference On Thermoelectrics, 1999), the disclosure of which is hereby incorporated herein in its entirety by reference.

Application of solid state thermoelectric cooling may be expected to improve the performance of electronics and sensors such as, for example, RF receiver front-ends, infra-red (IR) imagers, ultra-sensitive magnetic signature sensors, and/or superconducting electronics. Bulk thermoelectric materials typically based on p-$Bi_xSb_{2-x}Te_3$ and n-$Bi_2Te_{3-n}Se_x$ alloys may have figures-of-merit (ZT) and/or coefficients of performance (COP) which result in relatively poor thermoelectric device performance.

The performance of a thermoelectric device may be a function of the figure(s)-of-merit (ZT) of the thermoelectric material(s) used in the device, with the figure-of-merit being given by:

$$ZT = (\alpha^2 T \sigma / K_T),\quad \text{(equation 1)}$$

where $\alpha$, $T$, $\sigma$, $K_T$ are the Seebeck coefficient, absolute temperature, electrical conductivity, and total thermal conductivity, respectively. The material-coefficient Z can be expressed in terms of lattice thermal conductivity ($K_L$), electronic thermal conductivity ($K_e$) and carrier mobility ($\mu$), for a given carrier density (p) and the corresponding a, yielding equation (2) below:

$$Z = \alpha^2 \sigma / (K_L + K_e) = \alpha^2 / [K_L / (\mu \rho q) + L_0 T],\quad \text{(equation 2)}$$

where, $L_0$ is the Lorenz number (approximately $1.5 \times 10^{-8}$ $V^2/K^2$ in non-degenerate semiconductors). State-of-the-art thermoelectric devices may use alloys, such as p-$Bi_xSb_{2-x}Te_{3-y}Se_y$ (x~0.5, y=0.12) and n-$Bi_2(Se_yTe_{1-y})_3$ (y~0.05) for the 200 degree K to 400 degree K temperature range. For certain alloys, $K_L$ may be reduced more strongly than $\mu$ leading to enhanced ZT.

A ZT of 0.75 at 300 degree K in p-type $Bi_xSb_{2-x}Te_3$ (x~1) was reported forty years ago. See, for example Wright, D. A., Nature vol. 181, pp. 834 (1958). Since then, there has been relatively modest progress in the ZT of thermoelectric materials near 300 degree K (i.e., room temperature). A ZT of about 1.14 at 300 degree K for bulk p-type $(Bi_2Te_3)_{0.25}$ $(Sb_2Te_3)_{0.72}$ $(Sb_2Se_3)_{0.03}$ alloy has been discussed for example, in the reference by Ettenberg et al. entitled "A New N-Type And Improved P-Type Pseudo-Ternary $(Bi_2Te_3)$ $(Sb_2Te_3)(Sb_2Se_3)$ Alloy For Peltier Cooling," (Proc. of 15th Inter. Conf. on Thermoelectrics, IEEE Catalog. No. 96TH8169, pp. 52-56, 1996), the disclosure of which is hereby incorporated herein in its entirety by reference.

SUMMARY

According to some embodiments of the present invention, a temperature control system may include a thermoelectric device and a controller electrically coupled to the thermoelectric device. The controller may be configured to sense a first value of an electrical characteristic of the thermoelectric device, and to generate a first electrical control signal to pump heat through the thermoelectric device in response to sensing the first value of the electrical characteristic of the thermoelectric device. The controller may be further configured to sense a second value of the electrical characteristic of the thermoelectric device wherein the first and second values of the electrical characteristic are different. Responsive to sensing the second electrical characteristic of the thermoelectric device, the controller may be configured to generate a second electrical control signal to pump heat through the thermoelectric device, with the first and second electrical control signals being different.

The controller may be configured to sense the first and second electrical characteristics by sensing electrical signals generated by the thermoelectric device responsive to first and second heat gradients across the thermoelectric device. The controller may also be configured to generate the first electrical control signal so that heat is pumped through the thermoelectric device in a first direction, and to generate the second electrical control signal so that heat is pumped through the thermoelectric device in a second direction opposite the first direction. More particularly, the controller may be configured to generate the first electrical control signal so that a first electrical current flows through the thermoelectric device in a first direction, and to generate the second electrical control signal so that a second electrical current flows through the thermoelectric device in a second direction opposite the first direction.

The thermoelectric device may include a thermoelectric material such as bismuth telluride. More particularly, the thermoelectric device may include a P-type thermoelectric element and an N-type thermoelectric element electrically coupled in series and thermally coupled in parallel. Accordingly to other embodiments of the present invention, the thermoelectric device may include one or a plurality of thermoelectric elements of a same conductivity type.

In addition, a heat transfer structure may be thermally coupled to a first side of the thermoelectric device, and a temperature controlled medium may be thermally coupled to a second side of the thermoelectric device so that the thermoelectric device is thermally coupled between the heat transfer structure and the temperature controlled medium. More particularly, the temperature controlled medium may be a semiconductor substrate of an integrated circuit device, an optical device configured to emit and/or receive optical radiation, and/or a medical instrument (such as a blade, a scalpel, a probe, an implant, etc.) configured to contact living tissue. Moreover, the controller may be configured to generate the first and second electrical control signals to maintain a stable temperature of the temperature controlled medium; to provide a temperature ramp for the temperature controlled medium; and/or to provide a cyclical temperature profile for the temperature controlled medium.

According to some other embodiments of the present invention, a temperature controlled apparatus may include a heat transfer structure, a thermoelectric device, a temperature controlled medium, and a controller. The thermoelectric device may be thermally coupled between the heat transfer structure and the temperature controlled medium, and the controller may be electrically coupled to the thermoelectric device.

The controller may be configured to sense a first value of an electrical characteristic of the thermoelectric device, and to generate a first electrical control signal to pump heat through the thermoelectric device between the heat transfer structure and the temperature controlled medium in response to sensing the first value of the electrical characteristic of the thermoelectric device. The controller may be further configured to sense a second value of the electrical characteristic of the thermoelectric device with the first and second values of the electrical characteristic being different. In response to sensing the second electrical characteristic of the thermoelectric device, the controller may be configured to generate a second electrical control signal to pump heat through the thermoelectric device between the heat transfer structure and the temperature controlled medium with the first and second electrical control signals being different.

According to still other embodiments of the present invention, a method of controlling a thermoelectric device may include sensing an electrical characteristic of the thermoelectric device, and generating an electrical control signal to pump heat through the thermoelectric device in response to sensing the electrical characteristic of the thermoelectric device. For example, sensing the electrical characteristic may include sensing an electrical signal generated by the thermoelectric device responsive to a heat gradient across the thermoelectric device.

Generating the electrical control signal may include generating a first electrical control signal responsive to a first value of the electrical characteristic so that heat is pumped through the thermoelectric device in a first direction, and generating a second electrical control signal responsive to a second value of the electrical characteristic so that heat is pumped through the thermoelectric device in a second direction opposite the first direction, with the first and second values being different. Generating the first electrical control signal may include generating a first electrical current through the thermoelectric device in a first direction, and generating the second electrical control signal may include generating a second electrical current through the thermoelectric device in a second direction opposite the first direction.

The thermoelectric device may include a thermoelectric material such as bismuth telluride. For example, the thermoelectric device may include a P-type thermoelectric element and an N-type thermoelectric element electrically coupled in series and thermally coupled in parallel.

According to yet other embodiments of the present invention, a method of controlling a thermoelectric device may include sensing a first value of an electrical characteristic of the thermoelectric device, and after sensing the first value of the electrical characteristic, generating a first electrical control signal to pump heat through the thermoelectric device in response to sensing the first value of the electrical characteristic of the thermoelectric device. After generating the first electrical control signal, a second value of the electrical characteristic of the thermoelectric device may be sensed with the first and second values of the electrical characteristic being different. After sensing the second value of the electrical characteristic, a second electrical control signal may be generated to pump heat through the thermoelectric device in response to sensing the second electrical characteristic of the thermoelectric device, with the first and second electrical control signals being different.

Sensing the first and second electrical characteristics may include sensing electrical signals generated by the thermoelectric device responsive to first and second heat gradients across the thermoelectric device. Generating the first electrical control signal may include generating the first electrical control signal so that heat is pumped through the thermoelectric device in a first direction, and generating the second electrical control signal may include generating the second electrical control signal so that heat is pumped through the thermoelectric device in a second direction opposite the first direction. Generating the first electrical control signal may include generating a first electrical current through the thermoelectric device in a first direction, and generating the second electrical control signal may include generating a second electrical current through the thermoelectric device in a second direction opposite the first direction.

The thermoelectric device may include a thermoelectric material such as bismuth telluride. More particularly, the thermoelectric device may include a P-type thermoelectric element and an N-type thermoelectric element electrically coupled in series and thermally coupled in parallel.

BRIEF DESCRIPTION OF THE DRAWINGS

FIGS. 3A and 3B are respective cross sectional and plan views of a probe including a TE device according to some embodiments of the present invention.

FIGS. 4A and 4B are respective cross sectional and plan views of a probe including a TE device according to some embodiments of the present invention.

FIG. 8A is a plan view of a probe for a TE device according to some embodiments of the present invention.

FIG. 8B is a longitudinal cross section of the probe of FIG. 8A taken along section line B-B' according to some embodiments of the present invention.

FIG. 11 illustrates an expression that can be used to determine a temperature response to heat injected into and/or removed from a living body according to some embodiments of the present invention.

DETAILED DESCRIPTION

Figure 1A:
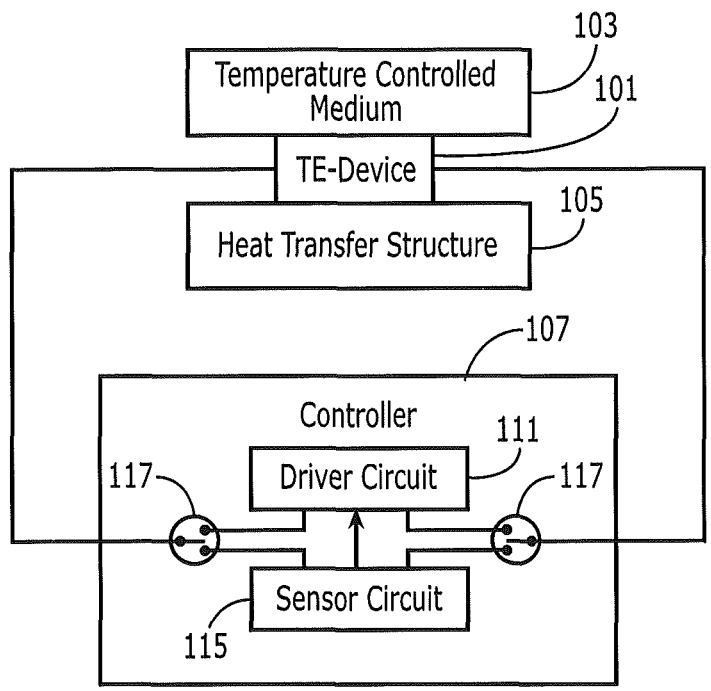
FIG. 1A is a block diagram of a temperature controlled apparatus according to some embodiments of the present invention.

The present invention is described more fully hereinafter with reference to the accompanying drawings, in which embodiments of the present invention are shown. This invention may, however, be embodied in many different forms and should not be construed as limited to the embodiments set forth herein. Rather, these embodiments are provided so that this disclosure will be thorough and complete, and will fully convey the scope of the present invention to those skilled in the art. In the drawings, the sizes and relative sizes of layers and regions may be exaggerated for clarity. Like numbers refer to like elements throughout.

It will be understood that when an element or layer is referred to as being "on", "connected to" or "coupled to" another element or layer, it can be directly on, connected or coupled to the other element, or layer or intervening elements or layers may be present. In contrast, when an element is referred to as being "directly on," "directly connected to" or "directly coupled to" another element or layer, there are no intervening elements or layers present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms.

These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath", "below", "lower", "above", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly. Also, as used herein, "lateral" refers to a direction that is substantially orthogonal to a vertical direction.

The terminology used herein is for the purpose of describing particular embodiments only, and is not intended to be limiting of the present invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments of the present invention are described herein with reference to cross-section illustrations that are schematic illustrations of idealized embodiments (and intermediate structures) of the invention. As such, variations from the shapes of the illustrations as a result, for example, of manufacturing techniques and/or tolerances, are to be expected. Thus, embodiments of the present invention should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of the present invention.

Unless otherwise defined, all terms (including technical and scientific terms) used herein have the same meaning as commonly understood by one of ordinary skill in the art to which this invention belongs. Accordingly, these terms can include equivalent terms that are created after such time. It will be further understood that terms, such as those defined in commonly used dictionaries, should be interpreted as having a meaning that is consistent with their meaning in the present specification and in the context of the relevant art, and will not be interpreted in an idealized or overly formal sense unless expressly so defined herein. All publications, patent applications, patents, and other references mentioned herein are incorporated by reference in their entirety.

As shown in FIG. 1A, a temperature controlled apparatus according to some embodiments of the present invention may include a thermoelectric (TE) device 101 thermally coupled between a temperature controlled medium 103 and a heat transfer structure 105. As shown, the thermoelectric device may also be electrically coupled with a controller 107. The thermoelectric device 101 may be a thermoelectric heat pump configured to pump heat from the temperature controlled medium 103 to the heat transfer structure 105 and/or to pump heat from the heat transfer structure 105 to the temperature controlled medium 103. The heat transfer structure 105 may include a thermal mass, a heat sink, a heat spreader, a heat pipe, a liquid line, a phase change material, a cold plate, etc.

The temperature controlled medium 103 may be any substrate, surface, device, instrument, etc. for which temperature control is desired. The temperature controlled medium 103, for example, may be a semiconductor substrate of an integrated circuit (IC) electronic device (including a plurality of interconnected electronic devices such as transistors, diodes, capacitors, inductors, resistors, etc.); a substrate of a discrete electronic device (including a single transistor, diode, capacitor, inductor, resistor, etc.); an optical device configured to emit and/or receive optical radiation; and/or a medical instrument (that is, a medical device such as a blade, scalpel, probe, implant, adhesive patch, hypodermic device, catheter, nerve stimulator, cochlear stimulator, vestibular system stimulator, etc.) configured to contact living tissue. In medical applications, the temperature controlled medium may include living tissue, such as a portion of a human body.

Moreover, the thermoelectric device 101 may be configured to act as both a heat pump and as a heat sensor. The thermoelectric device 101 may thus provide temperature feedback to the controller 107, and the controller 107 may use temperature feedback information from the thermoelectric device 101 to determine a control signal used to pump heat through the thermoelectric device 101. Accordingly, a separate temperature sensor may not be required thereby simplifying a structure of the temperature controlled apparatus.

Figure 1B:
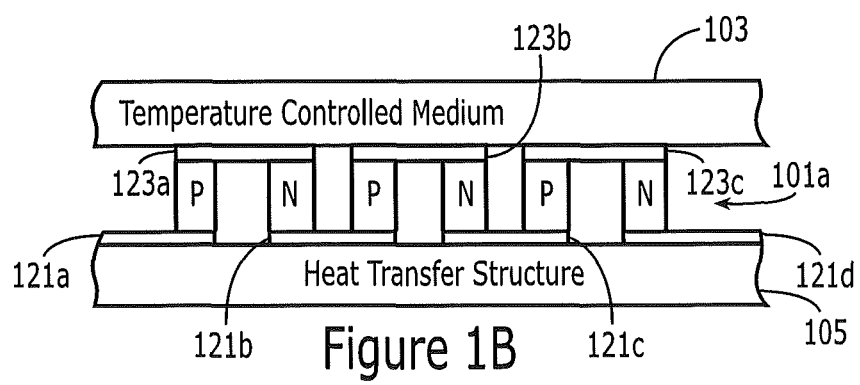
FIGS. 1B and 1C are cross sectional views illustrating thermoelectric devices according to different embodiments of the present invention.
Figure 1C:
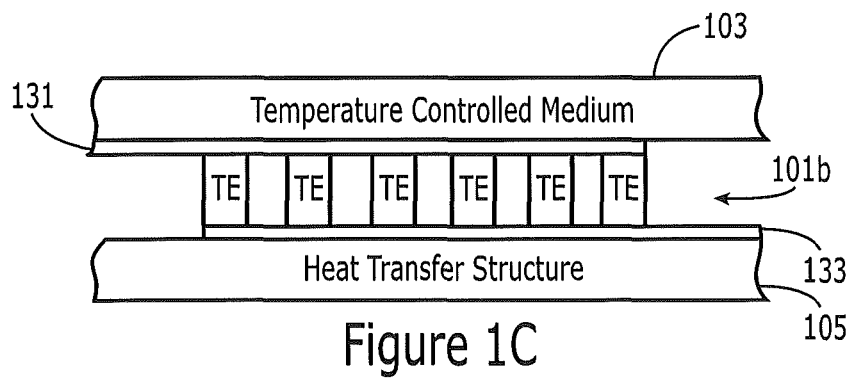

Thermoelectric (TE) devices 101a and 101b according to different embodiments of the present invention are respectively illustrated by way of example in FIGS. 1B and 1C. As shown in FIG. 1B, the TE device 101a may include a plurality of p-type TE elements P and n-type TE elements N electrically coupled in series through electrically conductive traces 121a-d and 123a-c (such as copper traces). More particularly, the p-type and n-type TE elements P and N may be alternatingly coupled so that current flows in a same first direction through all of the p-type TE elements P and in a same second direction (opposite the first direction) through all of the n-type TE elements N. Moreover, the electrically conductive traces 121a and 121d may provide electrical coupling to the controller 107. Accordingly, the p-type and n-type TE elements may be electrically coupled in series between terminals of the controller 107, and thermally coupled in parallel between the temperature controlled medium 103 and the heat transfer structure 105.

By generating an electrical current through the TE elements P and N having a first polarity between the electrically conductive traces 121a and 121d responsive to an electrical control signal generated by the controller 107, heat can be pumped from the temperature controlled medium 103 to the heat transfer structure 105 to thereby cool the temperature controlled medium 103. By generating an electrical current through the TE elements P and N having a second polarity (opposite the first polarity) between the electrically conductive traces 121a and 121d responsive to an electrical control signal generated by the controller 107, heat can be pumped from the heat transfer structure 105 to the temperature controlled medium 103 to thereby heat the temperature controlled medium 103. By sensing an electrical characteristic of the TE device 101a (e.g., a voltage across the TE device 101a, a current through the TE device 101a, and/or a resistance of the TE device 101a), a temperature gradient across the TE device 101a and/or a temperature of the temperature controlled medium 103 may be determined.

Each of the p-type and n-type TE elements P and N may include a layer of a thermoelectric material such as bismuth telluride ($Bi_2Te_3$). Each of the TE elements P and N may be electrically and mechanically coupled to respective traces 121a-d and 123a-c, for example, using solder together with a barrier metal, an adhesion metal, and/or other metallization layers. Materials, formation, and/or assembly of TE elements/structures are discussed, for example, in: U.S. Pat. Pub. No. 2003/0099279 entitled "Phonon-Blocking, Electron-Transmitting Low-Dimensional Structures"; U.S. Pat. Pub. No. 2007/0028956 entitled "Methods Of Forming Thermoelectric Devices Including Superlattice Structures Of Alternating Layers With Heterogeneous Periods And Related Devices"; U.S. Pat. Pub. No. 2006/0086118 entitled "Thin Film Thermoelectric Devices For Hot-Spot Thermal Management In Microprocessors And Other Electronics"; U.S. Pat. Pub. No. 2006/0289052 entitled "Methods Of Forming Thermoelectric Devices Including Conductive Posts And/Or Different Solder Materials And Related Methods And Structures"; U.S. Pat. Pub. No. 2006/0289050 entitled "Methods Of Forming Thermoelectric Devices Including Electrically Insulating Matrixes Between Conductive Traces And Related Structures"; U.S. Pat. Pub. No. 2007/0215194 entitled "Methods Of Forming Thermoelectric Devices Using Islands Of Thermoelectric Material And Related Structures"; U.S. Pat. Pub. No. 2007/0089773 entitled "Methods Of Forming Embedded Thermoelectric Coolers With Adjacent Thermally Conductive Fields and Related Structures"; U.S. Pat. No. 6,300,150 entitled "Thin-Film Thermoelectric Device And Fabrication Method Of Same". U.S. Pat. No. 7,164,077 entitled "Thin-Film Thermoelectric Cooling And Heating Devices For DNA Genomic And Proteomic Chips, Thermo-Optical Switching Circuits, And IR Tags"; U.S. Pat. No. 7,235,735 entitled "Thermoelectric Devices Utilizing Double-Sided Peltier Junctions And Methods Of Making The Devices"; and International PCT Pub. No. WO/2005/074463 entitled "Thin Film Thermoelectric Devices For Power Conversion And Cooling". The disclosures of each of the above referenced patent publications and patents are hereby incorporated herein in their entirety by reference.

Each of the TE elements P and N may include a thin film layer of a thermoelectric material having a thickness (in a direction between the electrically conductive traces 121a-d and 123a-c) that is less than about 100 .mu.m (micrometers) and more particularly less than about 50 .mu.m (micrometers). Moreover, the layers of the thermoelectric material may have substantially single crystal and/or substantially oriented polycrystalline structures (e.g., formed by epitaxial growth), or amorphous structures (e.g., formed by sputtering). Accordingly, the TE device 101a and/or portions thereof may be manufactured using semiconductor processing techniques (e.g., epitaxial growth and/or sputtering). By using semiconductor processing techniques to manufacture a thin film TE device, the thin film TE device may be more easily isolated to accommodate biocompatibility for medical applications.

As shown in FIG. 1C, the TE device 101b may include a plurality of TE elements TE of a same conductivity type (e.g., either p-type or n-type) electrically coupled in parallel between electrically conductive traces 131 and 133 (such as copper traces). Accordingly, the TE elements coupled so that current flows in a same direction through all of the TE elements. Moreover, the electrically conductive traces 131 and 133 may provide electrical coupling to the controller 107. Accordingly, the TE elements may be electrically coupled in parallel between terminals of the controller 107, and thermally coupled in parallel between the temperature controlled medium 103 and the heat transfer structure 105. While the TE device 101b of FIG. 1C is shown by way of example with a plurality of TE elements electrically coupled in parallel between the conductive traces 131 and 133, the TE device 101b may be implemented with a single TE element electrically coupled between the conductive traces 131 and 133.

By generating an electrical current through the TE elements having a first polarity between the electrically conductive traces 131 and 133 responsive to an electrical control signal generated by the controller 107, heat can be pumped from the temperature controlled medium 103 to the heat transfer structure 105 to thereby cool the temperature controlled medium 103. By generating an electrical current through the TE elements having a second polarity (opposite the first polarity) between the electrically conductive traces 131 and 133 responsive to an electrical control signal generated by the controller 107, heat can be pumped from the heat transfer structure 105 to the temperature controlled medium 103 to thereby heat the temperature controlled medium 103. By sensing an electrical characteristic of the TE device 101b (e.g., a voltage across the TE device 101b, a current through the TE device 101b, and/or a resistance of the TE device 101b), a temperature gradient across the TE device 101b and/or a temperature of the temperature controlled medium 103 may be determined.

Each of the TE elements may include a layer of a thermoelectric material such as bismuth telluride ($Bi_2Te_3$). Each of the TE elements may be electrically and mechanically coupled to respective traces 131 and 133, for example, using solder together with a barrier metal, an adhesion metal, and/or other metallization layers. Materials, formation, and/or assembly of TE elements/structures are discussed, for example, in: U.S. Pat. Pub. No. 2003/0099279 entitled "Phonon-Blocking, Electron-Transmitting Low-Dimensional Structures"; U.S. Pat. Pub. No. 2007/0028956 entitled "Methods Of Forming Thermoelectric Devices Including Superlattice Structures Of Alternating Layers With Heterogeneous Periods And Related Devices"; U.S. Pat. Pub. No. 2006/0086118 entitled "Thin Film Thermoelectric Devices For Hot-Spot Thermal Management In Microprocessors And Other Electronics"; U.S. Pat. Pub. No. 2006/0289052 entitled "Methods Of Forming Thermoelectric Devices Including Conductive Posts And/Or Different Solder Materials And Related Methods And Structures"; U.S. Pat. Pub. No. 2006/0289050 entitled "Methods Of Forming Thermoelectric Devices Including Electrically Insulating Matrixes Between Conductive Traces And Related Structures"; U.S. Pat. Pub. No. 2007/0215194 entitled "Methods Of Forming Thermoelectric Devices Using Islands Of Thermoelectric Material And Related Structures"; U.S. Pat. Pub. No. 2007/0089773 entitled "Methods Of Forming Embedded Thermoelectric Coolers With Adjacent Thermally Conductive Fields and Related Structures"; U.S. Pat. No. 6,300,150 entitled "Thin-Film Thermoelectric Device And Fabrication Method Of Same"; U.S. Pat. No. 7,164,077 entitled "Thin-Film Thermoelectric Cooling And Heating Devices For DNA Genomic And Proteomic Chips, Thermo-Optical Switching Circuits, And IR Tags"; U.S. Pat. No. 7,235,735 entitled "Thermoelectric Devices Utilizing Double-Sided Peltier Junctions And Methods Of Making The Devices"; and International PCT Pub. No. WO/2005/074463 entitled "Thin Film Thermoelectric Devices For Power Conversion And Cooling". The disclosures of each of the above referenced patent publications and patents are hereby incorporated herein in their entirety by reference.

Each of the TE elements TE of FIG. 1C may include a thin film layer of a thermoelectric material having a thickness (in a direction between the electrically conductive traces 131a-d and 133a-c) that is less than about 100 .mu.m (micrometers) and more particularly less than about 50 .mu.m (micrometers). Moreover, the layers of the thermoelectric material may have substantially single crystal and/or substantially oriented polycrystalline structures (e.g., formed by epitaxial growth), or amorphous structures (e.g., formed by sputtering). Accordingly, the TE device 101b and/or portions thereof may be manufactured using semiconductor processing techniques (e.g. epitaxial growth and/or sputtering). By using semiconductor processing techniques to manufacture a thin film TE device, the thin film TE device may be more easily isolated to accommodate biocompatibility for medical applications.

As shown in FIG. 11A, the controller 101 may include a driver circuit 111 and a sensor circuit 115 that may be separately coupled to the thermoelectric device 101 through switches 117. When the switches 117 couple the driver circuit 111 to the thermoelectric device 101, the driver circuit 111 may generate a control signal that causes the thermoelectric device 101 to pump heat between the temperature controlled medium 103 and the heat transfer structure 105. When the switches 117 couple the sensor circuit 115 to the thermoelectric device 101, the sensor circuit 115 may sense a value of an electrical characteristic of the thermoelectric device 101 with the electrical characteristic of the thermoelectric device 101 being indicative of a temperature gradient across the thermoelectric device 101 and/or a temperature of the temperature controlled medium 103. The controller 111 can thus control operation of the thermoelectric device 111 using feedback from the thermoelectric device 101.

According to some embodiments of the present invention, the switches 117 may couple the driver circuit 111 to the TE device 101 during heat pump periods to provide heat pumping interrupted by brief sensing intervals when the switches 117 couple the sensor circuit 115 to the TE device 101. During a first sensing interval, for example, the sensor circuit 115 may be electrically coupled with the TE device 101 through switches 117 to sense a first value of an electrical characteristic of the TE device 101. During a first drive period following the first sense interval, the driver circuit 111 may be electrically coupled with the TE device 101 through switches 117 to generate a first electrical control signal to pump heat through the thermoelectric device 101 between the heat transfer structure 105 and the temperature controlled medium 103 in response to sensing the first value of the electrical characteristic of the thermoelectric device. During a second sensing interval following the first drive period, the sensor circuit 115 may be electrically coupled with the TE device 101 through switches 117 to sense a second value of an electrical characteristic of the TE device 101, and the first and second values of the electrical characteristic may be different. During a second drive period following the second sense interval, the driver circuit 111 may be electrically coupled with the TE device 101 through switches 117 to generate a second electrical control signal to pump heat through the thermoelectric device between the heat transfer structure and the temperature controlled medium in response to sensing the second electrical characteristic of the thermoelectric device.

According to some other embodiments of the present invention, the driver circuit 111 and the sensor circuit 115 may be electrically coupled in parallel with the TE device 101 without the switches 117 so that interruption of the control signal is not required during sensing intervals. The sensor circuit 115, for example, may be configured to sense a voltage across the TE device 101 and a current through the TE device 101 to determine a temperature gradient across the TE device 101 without interrupting a current through the TE device 101 generated responsive to a control signal from the driver circuit 111. A continuous control signal generated by the driver circuit 111 may thus be varied responsive to the sensor circuit 115.

As the value of the electrical characteristic changes (due to changing temperatures of the temperature controlled medium 103), the controller 107 may change a control signal generated by the driver circuit 111 during different drive periods to maintain a desired temperature of the temperature controlled medium 103. During sensing intervals, for example, the sensor circuit 115 may sense an electrical characteristic of the TE device 101 such as a voltage generated by the TE device 101, a current generated by the TE device 101, a resistance of the TE device 101, etc. During drive periods, the driver circuit 111 may provide a drive current through the TE device 101 with increased magnitudes of the driver current providing increased heat pumping, with decreased magnitudes of the driver current providing decreased heat pumping, with a first polarity of the driver current providing cooling of the temperature controlled medium 103, and with a second polarity (opposite the first polarity) of the driver current providing heating of the temperature controlled medium 103. The electrical control signals may differ, for example, so that a current through the TE device 101 is either on or off during different drive periods; so that currents through the TE device 101 have different magnitudes during different drive periods; so that currents through the TE device 101 have different polarities during different drive periods; and/or so that currents through the TE device 101 have different duty cycles during different drive periods.

With a semiconductor substrate of an integrated circuit electronic device, a medical probe, and/or living tissue as the temperature controlled medium 103, for example, the controller 107 may be configured to provide that the TE device 101 cools a hot spot of the temperature controlled medium 103 when a temperature gradient across the TE device 101 exceeds a threshold. Accordingly, the controller 107 may be configured to provide cooling only. With an optical electronic device as the temperature controlled medium 103, for example, the controller 107 may be configured to provide that the TE device 101 heats the temperature controlled medium 103 when a temperature gradient across the TE device is less than a low temperature threshold and to provide that the TE device 101 cools the temperature controlled medium 103 when a temperature gradient across the TE device 101 is greater than a high temperature threshold. Accordingly, the controller 107 may be configured to provide heating and cooling to maintain a relatively stable temperature. With a medical scalpel as the temperature controlled medium 103, for example, the controller 107 may be configured to provide that the TE device 101 heats the scalpel when a temperature gradient across the TE device 101 is less than a threshold. Accordingly, the controller 107 may be configured to provide heating only.

Figure 2:
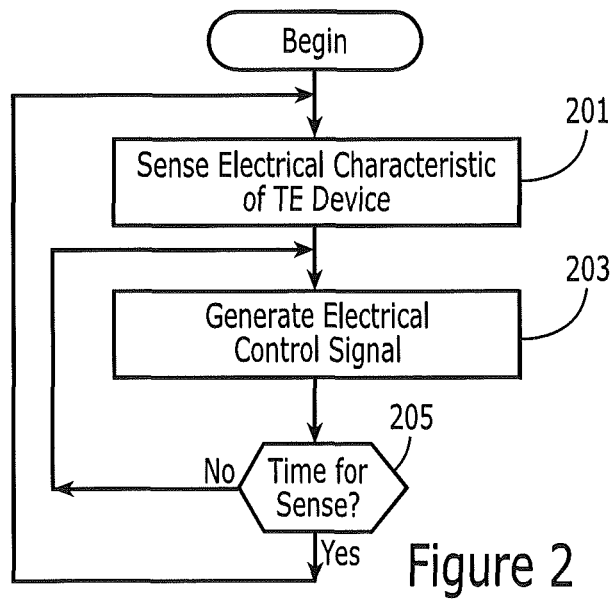
FIG. 2 is a flow chart illustrating operations of controlling a thermoelectric device according to some embodiments of the present invention.

FIG. 2 is a flow chart illustrating operations of controlling the TE device 101 according to some embodiments of the present invention. At block 201, the controller 107 may sense a first value of an electrical characteristic of the thermoelectric device 101 (e.g., representative of a temperature gradient across the TE device 101 and/or a temperature of the temperature controlled medium 103). At block 203, the controller 107 may generate an electrical control signal (e.g., a current through the TE device 101) to pump heat through the thermoelectric device 101 between the heat transfer structure 105 and the temperature controlled medium 103 in response to sensing the first value of the electrical characteristic of the thermoelectric device at block 201. At block 205, the controller 107 may determine if the time has come for a next sense operation. By way of example, sense operations at block 201 may be performed periodically at set time intervals, and the electrical control signal may remain unchanged at block 203 until a subsequent sense operation is performed at block 201. If a same electrical characteristic is sensed during first and second consecutive sense operations at block 201, the electrical control signal generated at block 203 may remain unchanged after the second consecutive sense operation. If the electrical characteristic sensed during first and second consecutive sense operations at block 201 changes, the electrical control signal generated at block 203 may change after the second consecutive sense operation.

According to some embodiments of the present invention, the electrical control signal generated at block 203 may be interrupted when sensing the electrical characteristic of the TE device 101 at block 201. According to other embodiments of the present invention, the electrical characteristic of the TE device 101 may be sensed at block 201 without interrupting the electrical control signal generated at block 203. The electrical control signals generated at block 203 may differ, for example, so that a current through the TE device 101 is either on or off during different drive periods; so that currents through the TE device 101 have different magnitudes during different drive periods; so that currents through the TE device 101 have different polarities during different drive periods; and/or so that currents through the TE device 101 have different duty cycles during different drive periods. Sensing the electrical characteristic of the TE device 101 at block 201 may include sensing a current through the TE device 101; sensing a voltage across the TE device 101; sensing a current through the TE device 101 and a corresponding voltage across the TE device 101; sensing a resistance of the TE device 101; etc. Moreover, the electrical characteristic of the TE device 101 sensed at block 201 may be representative of a temperature gradient across the TE device 101 and/or a temperature of the temperature controlled medium 103.

According to some embodiments of the present invention, the controller 107 may be configured to generate the electrical control signal at block 203 to maintain a stable temperature for the temperature controlled medium 103. For example, the controller 107 may be configured to generate the electrical control signal at block 203 to provide that the temperature controlled medium 103 does not exceed a high temperature threshold, to provide that the temperature controlled medium 103 is maintained between high and low temperature thresholds, or to provide that the temperature controlled medium 103 is maintained above a low temperature threshold. According to some other embodiments of the present invention, the controller 107 may be configured to generate the electrical control signal at block 203 to provide a temperature ramp for the temperature controlled medium 103. According to still other embodiments of the present invention, the controller 107 may be configured to generate the electrical control signal at block 203 to provide a cyclical temperature profile for the temperature controlled medium 103.

According to some embodiments of the present invention, a thermoelectric (TE) cooling/heating device (also referred to as a Peltier cooling device) may provide a cold probe that can be used for medical and/or other purposes. Such a device can be used to create local cold and/or hot areas for medical applications. A TE cooling/heating device, for example, may be used to provide a scalpel with a controlled temperature at the blade, and/or to provide a medical implant that delivers controlled temperatures to localized areas in the human body. An insertable or implantable TE cooling/heating device may be used to provide medical treatment such as to cool nerves, tumors, and/or portions of the brain, to reduce pain, treat cancer, and/or to stop/reduce seizures. Use of thermoelectric devices to stop seizures is discussed, for example, in the publication by Maria Fontanazza entitled "A Cooler Way To Stop Seizures" (Medical Device & Diagnostic Industry Magazine, October 2005), the disclosure of which is hereby incorporated herein in its entirety by reference.

According to still other embodiments of the present invention, the temperature control system may be a nerve stimulator, capable of both activating and inhibiting neural transmission. Nerve stimulators according to the present invention may be provided in a variety of forms. In some embodiments, a nerve stimulator may be configured in the form of a probe or an elongate probe. Such configurations have been developed for electrical nerve stimulation and are well known. Thus, nerve stimulation probes of the present invention can be configured as vagal nerve stimulation probes, deep brain stimulation probes, motor cortex stimulation probes, peripheral nerve stimulation probes, brainstem stimulation probes, spinal cord stimulation probes, etc. Alternatively, a nerve stimulator according to the present invention may be configured to be insertable into the ear canal of a subject. Such a stimulator may conformably engage the subject's ear canal.

In further embodiments of the present invention, the temperature control system may be configured as a cochlear stimulator. A cochlear stimulator may be configured to be inserted into the cochlea of a subject with the temperature controlled medium positioned so as to stimulate a plurality of ganglion cells in the basal region of the cochlea. Such a cochlear stimulator can be constructed with known elements and in accordance with known designs, modified to incorporate a thermoelectric device as described herein. See, e.g., U.S. Pat. No. 6,038,484 to Kuzma.

In still further embodiments of the present invention, the temperature control system may be configured as a vestibular system stimulator. A vestibular system stimulator according to the present invention may be configured to deliver caloric vestibular stimulation to a subject. Such a stimulator may be configured to be insertable in the ear canal of a subject, and may optionally be designed to conformably engage the subject's ear canal.

Any suitable stimulation signal may be utilized in accordance with the present invention, including but not limited to continuous stimulation, intermittent stimulation and cyclic stimulation. Such cyclic stimulation (e.g., heat then off and repeat, cool then off and repeat, heat then cool then off and repeat, etc.) may be a uniform waveform, randomized, stochastic, etc., with each cycle lasting from about one minute to about ten minutes in duration. Intermittent and/or cyclic stimulation may be accomplished by providing thermal pulses to the temperature controlled medium. Such thermal pulses may be from about one-half second to about two minutes in duration. Such thermal pulses may be separated in time by about one-half second to about five minutes.

The magnitude of the thermal stimulus utilized will depend upon factors such as the tissue being contacted (both the tissue type and the volume of the tissue), the duration of the stimulus, etc. In some embodiments, the tissue adjacent to the temperature controlled medium is cooled at least 1, 2, 3, or 4 degrees Centigrade, up to 5, 10, or 20 degrees Centigrade, or more. In some embodiments, the tissue adjacent to the temperature controlled medium is heated at least 1, 2, 3, or 4 degrees Centigrade, up to 5, 10, or 20 degrees Centigrade, or more. Those skilled in the art will appreciate how to select appropriate limits on duration/magnitude of stimulus to avoid tissue damage.

FIG. 3A is a cross sectional view of a probe including a TE device 301 according to some embodiments of the present invention, and FIG. 3B is a plan view of the probe of FIG. 3A. In the probe of FIGS. 3A and 3B, the TE device 301 may be provided on a metal probe 303 that acts as a heat transfer structure, and the electrically conductive traces 305 may provide electrical coupling between the TE device 301 and a controller (not shown in FIGS. 3A and 3B) such as the controller 107 discussed above with respect to FIGS. 1A and 2. Moreover, an electrically insulating layer 307 may be provided between the electrically conductive traces 305 and the metal probe 303, and an insulating underfill 317 may be provided on/between TE elements.

The TE device 301 may include a plurality of n-type TE elements 309 and p-type TE elements 311 electrically coupled in series and thermally coupled in parallel as discussed above with respect to FIG. 1B. Moreover, a header 315 may provide electrical coupling between pairs of n-type and p-type thermoelectric elements of the TE device 301. A thickness of the TE device 301 (including the header 315) may be about 100 .mu.m (micrometers) or less. As shown in FIGS. 3A and 3B, the TE device 301 may be provided on a surface of the metal probe 303. According to other embodiments of the present invention, the TE device 301 may be embedded in a recess in a surface of the metal probe 303. As shown in FIGS. 3A and 3B, the TE device 301 may be oriented so that the TE elements 309 and 311 and the header 315 are parallel with respect to a surface of the metal probe 303. According to other embodiments of the present invention, the TE device 301 may be oriented so that the TE elements 309 and 311 and the header 315 are oriented at a non-parallel angle (e.g., 90 degrees) with respect to a surface of the metal probe 303.

In the probe of FIGS. 3A and 3B, electrical current may flow in series through the n-type and p-type TE elements 309 and 311 to pump heat in parallel from the cold side header 315 to the hot side metal probe 303. In other words, the n-type and p-type TE elements 309 and 311 are electrically connected in series so that current through the p-type TE elements 311 flows in a direction opposite to a direction that current flows through the n-type TE elements 309. The n-type TE elements 309 and the p-type TE elements are thermally coupled in parallel, however, so that heat is pumped from the cold side through the n-type and p-type thermoelectric elements to the hot side and into the probe 303 acting as a heat transfer structure. In a medical application, the TE device 301 may be placed on/adjacent living tissue to be cooled so that the living tissue acts as the temperature controlled medium discussed above with respect to FIGS. 1A, 1B, 1C, and 2.

Figure 5:
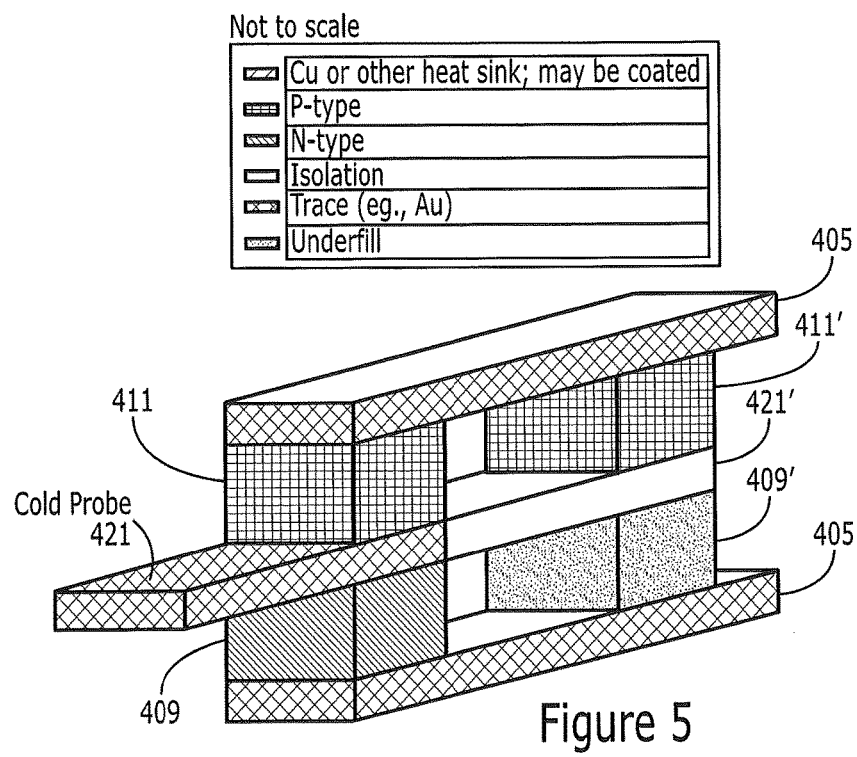
FIG. 5 is a greatly enlarged view of the TE device of FIGS. 4A and 4B.

According to other embodiments of the present invention, both electrical current and heat may flow in series. For example, the temperature controlled medium may be provided between n-type and p-type TE elements. As shown in FIGS. 4A, 4B, and 5, a TE device 401 may be provided on a metal probe 403 that acts as a heat transfer structure, and the electrically conductive traces 405 may provide electrical coupling between the TE device 401 and a controller (not shown in FIGS. 4A, 4B, and 5) such as the controller 107 discussed above with respect to FIGS. 1A and 2. Moreover, an electrically insulating layer 407 may be provided between the electrically conductive traces 405 and the metal probe 403, and an insulating underfill 417 may be provided on/between TE elements.

The TE device 401 may include an n-type TE element 409 and a p-type TE element 411 electrically coupled in series and thermally coupled to pump heat from opposite sides of the cold probe 421. As shown in FIGS. 4A, 4B, and 5, electrical current may flow in series through the n-type TE element 409, the cold probe 421, and the p-type TE element 411 between the electrically conductive traces 405. FIG. 5 is a greatly enlarged view of the TE device 401 and cold probe 421 of FIGS. 4A and 4B. As shown in FIG. 5, the cold probe 421 may be extended (indicated by dotted lines and the reference 421') to allow additional n-type and p-type TE elements 409' and 411'.

Accordingly, heat may be pumped from the cold probe 421 through the n-type and p-type TE elements 409 and 411 to the electrically conductive traces 405 on opposite sides of the cold probe 421. Portions of the cold probe 421 extending beyond the TE elements 409 and 411 may be shaped as a blade to provide a thermoelectrically cooled (or heated) scalpel. According to other embodiments of the present invention, portions of the probe 421 extending beyond the TE elements 409 and 411 may be shaped to provide a probe that may be inserted with precision in a human body to provide heating and/or cooling.

According to embodiments of the present invention, a TE device may be used to provide cooling, heating, and/or temperature control at a portion of a human body (or other living tissue) to provide medical treatment in areas such as neurological seizure control, pain management, transdermal delivery of pharmaceutical agents, and/or caloric stimulation of retrocortical cerebral enhancement. Such medical TE devices may be implantable, insertable, hypodermic, attachable, and/or wearable. Moreover, a medical TE device may provide both heat pumping functionality and temperature feedback functionality as discussed above with respect to FIGS. 1A, 1B, 1C, and 2.

In general, a cooling device may include a cold surface at the tip of a probe with a sub-ambient temperature that is maintained using a solid-state device, such as a TE device (also referred to as a thermoelectric cooler or TEC), which in turn is attached to a body of a thermal mass configured to retain, transfer, transport and/or remove the heat from the hot-side of the solid-state device to the surrounding body tissues and/or ambient heat sink.

According to embodiments of the present invention, heat may be removed from the TE device to a surrounding heat-sink without incurring significant thermal damage to tissues between the TE device and an internal or external heat-sink. This heat removal may be accomplished by maintaining an amount of heat dissipation from an exposed surface(s) of the device to within a pre-determined level of heat-flux and temperature that can be tolerated by the tissue. Different embodiments of the present invention may include transporting heat away from a hot-side of a TEC to either a thermal mass and/or a heat sink, and diluting a level of heat density at a surface that is in intimate contact with the tissues. Dilution of heat may occur in spatial and/or temporal dimensions.

With an implantable TE heating/cooling device, heat-energy may be absorbed and/or dispersed in such a way that, by the time that the heat-flow reaches the surrounding tissue(s), the heat-density is low enough that the surrounding tissues themselves may serve as a heat-sink. A thermal mass including materials of high-thermal-diffusivity and/or high-thermal-capacitance (i.e., phase change materials or PCM's) may be attached to a hot-side of the TE device to absorb and/or diffuse heat relatively uniformly throughout the mass.

Figure 6:
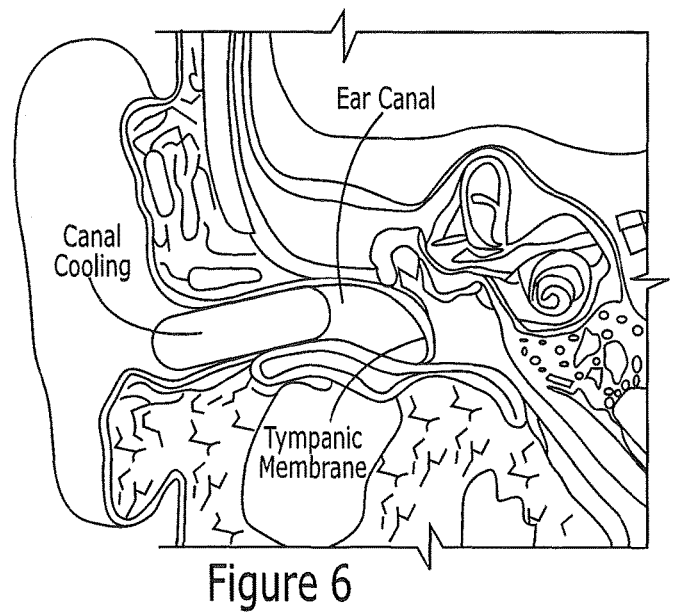
FIG. 6 is a picture illustrating a portion of a human ear canal that may be cooled for retrocortical cerebral enhancement according to some embodiments of the present invention.
Figures 7A, 7B:
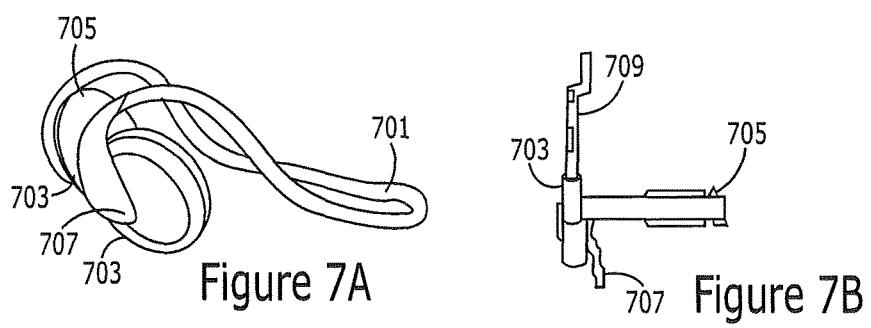
FIG. 7A is a plan view of an insertable and wearable TE cooling device implemented with an earphone shaped support that is worn on the head according to some embodiments of the present invention.
FIG. 7B is a cross sectional view of an earpad and probe of the cooling device of FIG. 7A according to some embodiments of the present invention.

As shown in FIG. 6, cooling of a human ear canal may be provided, for example, for retrocortical cerebral enhancement. As shown in FIGS. 7A and 7B, an insertable and wearable TE cooling device may be implemented with an earphone shaped support including a headband 701 and earpads 703 that are worn on the head. A TE cooling probe 705 may extend from an earpad 703 into the ear canal when worn, and the earpad 703 may include a passive heat sink 707 (such as a thermal mass or cold plate) and/or an active heat sink 709 (such as a heat pipe or a liquid line). Control circuitry and/or a power source (such as batteries) may also be provided in/on the earpads 703. The probe 705 may be provided as discussed above with respect to FIGS. 3A, 3B, 4A, 4B, and/or 5, or as discussed below with respect to other embodiments of the present invention.

Figure 8C:
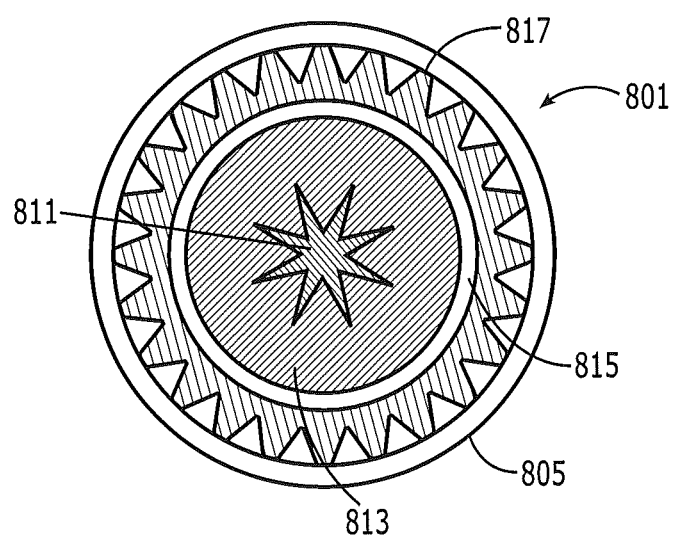
FIG. 8C is a circumferential cross section of the probe of FIGS. 8A and 8B taken along section line C-C' according to some embodiments of the present invention.
Figure 8D:
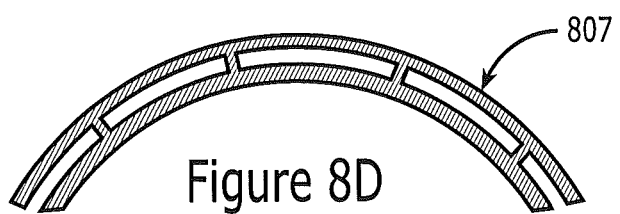
FIG. 8D is a greatly enlarged view of a portion of an adiabatic zone of the probe of FIG. 8A taken along section line C-C' according to some embodiments of the present invention.

FIG. 8A is a plan view of a probe 801 for a TE device according to some embodiments of the present invention. FIGS. 8B and 8C are respective longitudinal and circumferential cross sections of the probe of FIG. 8A. FIG. 8D is a greatly enlarged view of a portion of an adiabatic zone of the probe of FIG. 8A. Moreover, the probe 801 of FIGS. 8A-8D may be used as the probe of 705 of FIGS. 7A and 7B, and/or the probe 801 may be used as a medical implant.

As shown in FIGS. 8A-8D, the probe 801 may include a high thermal conductivity (high-k) cold tip 803 (such as a metal tip) and an outer shell 805 having an adiabatic zone 807. The adiabatic zone 807 may have a double shell with internal channels containing a coolant as shown in FIG. 8D. A TE device 809 may be provided as discussed above with respect to FIGS. 1A, 1B, and 1C with a cold-side in contact with the cold tip 803 and with a hot side in contact with a core of the probe 801. The core of the probe may include an inner core 811 and an outer core 813. The inner core 811 may provide a high thermal conductivity, and more particularly, the inner core 811 may include a phase change material with radial fins. The outer core 813 may include a phase change material and/or a high thermal conductivity material such as carbon graphite, a heat pipe, and/or a continuous vapour-deposited diamond (CVDD). The inner and/or outer cores 811 and/or 813 may be configured to disperse heat and/or to transport heat away from the hot side of the TE device 809 to an external heat sinking mechanism.

In addition, an insulating layer 815 may be provided between the core (811 and/or 813) and an inner shell 817. The insulating layer 815 may include electrical power and/or ground connections between the TE device 809 and a controller, and the inner shell 817 may include a low thermal conductivity material with a low touch temperature and a low-q dissipation. While not shown in FIGS. 8A-8D, a controller and power source may be provided within and/or outside the probe 801, and the controller may be configured to control operation of the TE device 809 as discussed above with respect to FIGS. 1A, 1B, 1C, and 2.

Figure 9A:
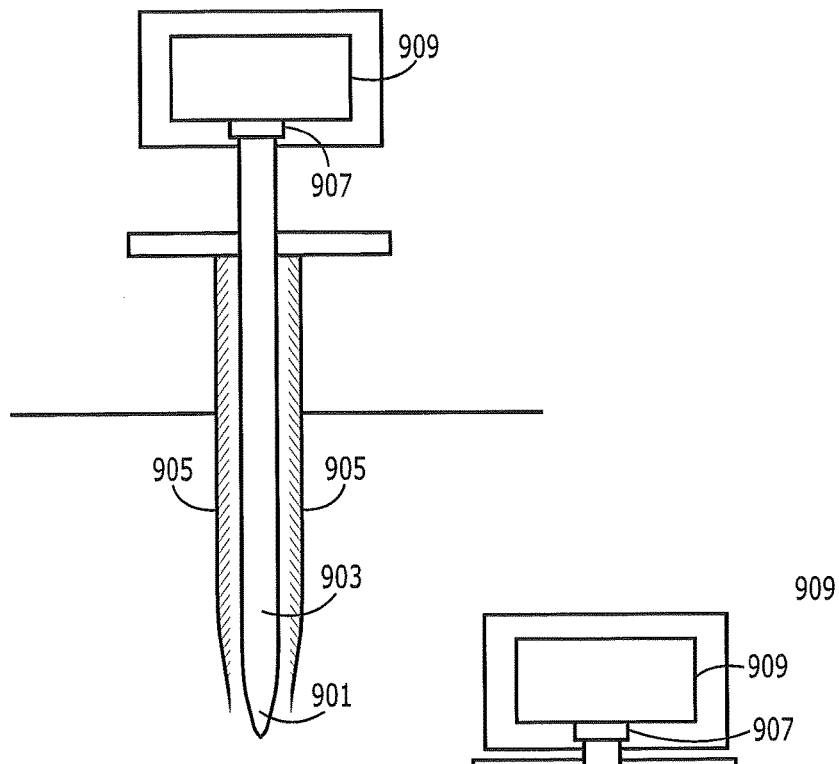
FIGS. 9A and 9B are cross sectional views of a medical hypodermic TE cooling device in respective retracted and inserted positions according to some embodiments of the present invention.
Figure 9B:
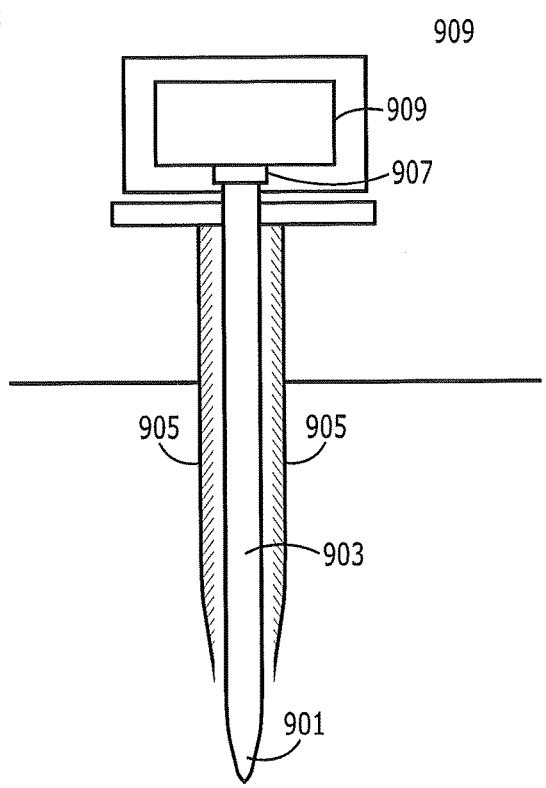

FIGS. 9A and 9B are cross sectional views of a medical hypodermic cooling device in respective retracted and inserted positions according to some embodiments of the present invention. In particular, a cold tip 901 may be provided at the end of a retractable/insertable high-k core 903 (e.g., a graphite or heat pipe core). Moreover, the core 903 may retractable and/or insertable within a low thermal conductivity (low-k) shell 905. A TE cooling device 907 may be provided between the core 903 and a heat transfer structure 909 (such as a phase change material, a thermal mass, and/or a heat sink) with a cold side of the TE device in thermal contact with the core 903 and with a hot side of the TE device in thermal contact with the heat transfer structure 909. While not shown in FIGS. 9A and 9B, a controller may be configured to control operation of the TE device 907 as discussed above with respect to FIGS. 1A, 1B, 1C, and 2. Accordingly, the core 903 and cold tip 901 may be maintained at a relatively low temperature and inserted into living tissue (e.g., inserted through skin into a human body) to cool a local target tissue of choice.

Figure 10A:
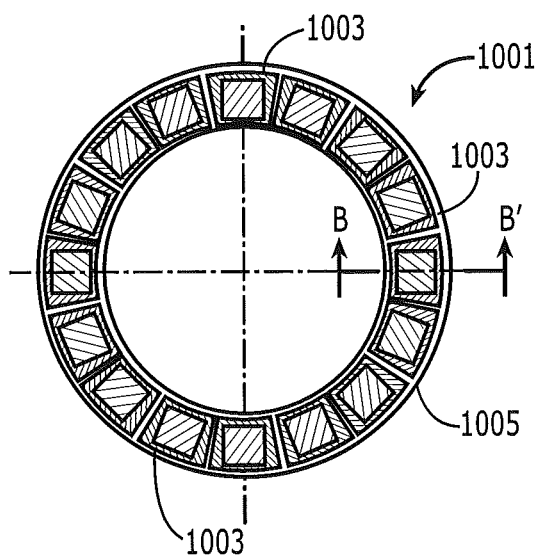
FIG. 10A is a plan view of a temperature control patch including a plurality of heating/cooling elements according to some embodiments of the present invention.
Figure 10B:
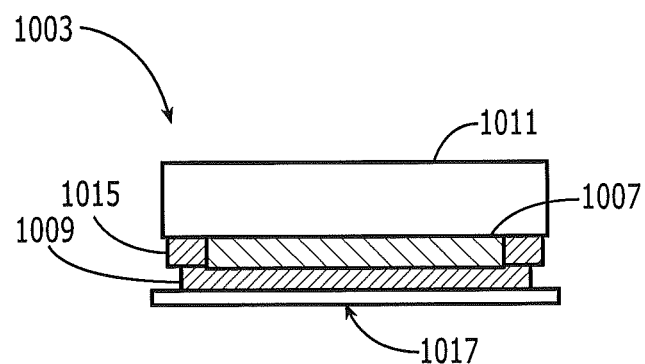
FIG. 10B is a cross sectional view of a single heating/cooling element from the temperature control patch taken along section line B-B' of FIG. 10A.

FIG. 10A is a plan view of an adhesive temperature control patch 1001 including a plurality of cooling/heating elements 1003 according to some embodiments of the present invention, and FIG. 10B is a cross sectional view of a single cooling/heating element 1003. Moreover, a flexible matrix 1005 may physically connect the plurality of cooling/heating elements 1003. According to some embodiments of the present invention, the temperature control patch 1001 may be attached to human skin to provide localized cooling of a portion of epidermis and/or dermis undergoing an incision. Such cooling may be useful to control physiological aspects of human responses during and/or after a medical procedure (by decreasing swelling, reducing itching, etc). According to other embodiments of the present invention, the temperature control patch 1001 may be used to provide heating. Such heating may be useful to increase blood flow to a portion of the epidermis and/or dermis, to stimulate nerves, to enhance drug delivery, etc.

As shown in FIG. 10B, a cooling/heating element 1003 may include a TE cooling/heating device 1007 between a heat transfer structure 1011 (such as a thermal mass or heat sink) and a high-k substrate 1009. In addition, an insulating underfill material 1015 may surround the TE cooling/heating device 1007, and an adhesive layer 1017 may provide a conformable and adhesive surface to be applied to skin.

FIG. 11 illustrates an expression that may be used to determine temperature responses to heat injected into and/or removed from a living body part (also referred to as a substrate). A temperature of the of the substrate (or body part) may be determined as a function of depth x and time t using the formula $T(x, t) - T_0$. Moreover, $q''$ may be either positive for heating or negative for cooling.

TE cooling/heating devices discussed above may use a control mechanism, internal and/or external, to monitor and/or maintain device functionalities within specifications and/or usage requirements. A size and/or performance of a thin-film TE cooling/heating device may enable an electrical circuit in which the TE cooling/heating device provides an integral function of the operation of the circuit. A micro-TE cooling/heating device can be a part of the circuit to influence its own performance through a feedback loop, for example, as discussed above with respect to FIGS. 1A and 2. According to some embodiments of the present invention, a TE cooling/heating device may or may not be physically attached to all or part of the rest of the electrical circuit and functions of the TE device may include heating, cooling, and/or power generation.

According to some embodiments of the present invention, a TE device may operate in a signal generating mode to sense a thermal gradient and to generate a current (or other electrical signal) in response to the temperature gradient. The current (or other electrical signal) may be used to influence operations of an electrical circuit (such as a controller), which in turn can control an operational characteristic(s) of the TE device when operating in a heating and/or cooling mode. Stated in other words, during a temperature sensing operation, a current generated by the TE device responsive to a heat gradient across the TE device may be used to determine a temperature of the surface being cooled. During a cooling operation, a current through the TE device may be controlled responsive to the temperature determined during the temperature sensing operation. The same TE device may thus provide both temperature sensing and cooling/heating.

According to some other embodiments of the present invention, a temperature sensitive device may be physically attached to the surface of a micro TE device, and the temperature sensitive device may also be electrically connected to the drive circuit (e.g., controller) of the TE device. The TE device (by way of its relatively fast response time) may rapidly influence the performance of the temperature sensitive device by heating and/or cooling, while feedback from the temperature sensitive device may modulate an amount of heating and/or cooling that the TE device does (e.g., a power transistor may actively cool and/or heat itself in advance of reaching a damaging or debilitating operating temperature). According to still other embodiments of the present invention, a TE device may rapidly switch from heating to cooling and/or from cooling to heating to achieve different operating characteristics.

Elements of a control circuit according to embodiments of the present invention may include:
1) a control circuit that resides on and/or within a medical probe and/or thermal control structure, residing either within or external to a living body;
2) a feedback sensor that measures temperature and/or heat flux either internally or externally to a thin film TE device using either an external sensor(s) (e.g., thermocouple) or an internal sensor(s) (i.e., the thin film TE device itself);
3) a control circuit (or controller) including a proportional-integral-derivative (PID) controller, where the PID controller uses a sensing mechanism internal and/or external to the thin film TE device to control the TE device;
4) a PID controller providing that a cooling/heating curve meets a desired cooling/heating curve profile, and the cooling/heating curve may be designed to meet a specific therapeutic need such as,
    a) a ramp to a specific temperature or heat flux which is then held in a steady state,
    b) a cycle including ramping to a first desired temperature or heat flux, maintaining the first desired temperature or heat flux for a period of time, and then ramping to a second desired temperature or heat flux and holding the second desired temperature or heat flux for a second period of time, and then repeating of the cycle to provide a wave form, and/or
    c) ramping within a cycle can be designed to achieve any type of cyclical wave form (e.g., sinusoidal, square wave, saw tooth, etc.).

By inserting brief off-duty periods (also referred to as sensing intervals), when the TE device is not driven with current to heat or cool, into any of the profiles mentioned above, a signal generating mode can be incorporated into the system using the TE device to sense a temperature and/or heat flux. During each off-duty period or sensing interval, the TE device itself may be used as a sensor/thermocouple where the output signal (which has been calibrated to the temperature and/or heat flux) is fed back to the controller to dynamically determine a profile of a next round of cooling/heating duty cycles (also referred to as drive periods). Use of the TE device to both heat/cool and to sense may be feasible because a response time constant of a micro TEC may be on the order about 10 ms or less.

As used herein, the term thermoelectric element includes a structure having a layer of a thermoelectric material (e.g., Bi.sub.2Te.sub.3) with a Seebeck coefficient sufficient to provide thermoelectric heat pumping (heating or cooling) responsive to an electrical current therethrough and/or electrical power generation responsive to a temperature gradient across the thermoelectric element. A thermoelectric element, for example, may include one or more P-N couples with a P-N couple having a P-type thermoelectric element and an N-type thermoelectric element electrically coupled in series and thermally coupled in parallel and configured to provide thermoelectric heating, cooling, and/or power generation. According to other embodiments of the present invention, a thermoelectric element may include a single layer of a thermoelectric material (either P-type or N-type) configured to provide thermoelectric heating, cooling, and/or power generation.

As discussed above TE devices may be used to provide heating, cooling, power generation, and/or temperature sensing according to embodiments of the present invention. While some embodiments may be discussed with respect a TE device(s) to provide cooling, it will be understood that the TE device(s) of such embodiments may also be used to provide heating, power generation, and/or temperature sensing. While some embodiments may be discussed with respect a TE device(s) to provide heating, it will be understood that the TE device(s) of such embodiments may also be used to provide cooling, power generation, and/or temperature sensing. While some embodiments may be discussed with respect a TE device(s) to provide power generation, it will be understood that the TE device(s) of such embodiments may also be used to provide heating, cooling, and/or temperature sensing.

While the present invention has been particularly shown and described with reference to embodiments thereof, it will be understood by those of ordinary skill in the art that various changes in form and details may be made therein without departing from the spirit and scope of the present invention as defined by the following claims.

That which is claimed:

1. A temperature control system comprising:
a thermoelectric device;
a controller electrically coupled to the thermoelectric device and configured to sense an electrical characteristic of the thermoelectric device;
a heat transfer structure thermally coupled to a first side of the thermoelectric device;
a temperature controlled medium thermally coupled to a second side of the thermoelectric device so that the thermoelectric device is thermally coupled between the heat transfer structure and the temperature controlled medium, wherein said temperature controlled medium comprises a medical instrument configured to contact living tissue; and
a temperature feedback sensor, wherein said controller is configured to generate a first electrical control signal to activate said thermoelectric device and said first electrical control signal is generated in response to a first value of the electrical characteristic of the thermoelectric device, wherein the electrical characteristic of the thermoelectric device comprises an electrical characteristic of the thermoelectric device indicating one of a temperature gradient across the thermoelectric device and a temperature of the temperature controlled medium.

2. The temperature control system of claim 1, wherein said electrical characteristic comprises a voltage across the thermoelectric device.

3. The temperature control system of claim 1, wherein said electrical characteristic comprises a current through the thermoelectric device.

4. The temperature control system of claim 1, wherein said electrical characteristic comprises a resistance of the thermoelectric device.

5. The temperature control system of claim 1, wherein said first electrical control signal is generated in response to temperature feedback data generated by the temperature feedback sensor.

6. The temperature control system of claim 1, wherein said controller is configured to generate a second electrical control signal to activate said thermoelectric device, said second electrical signal being generated in response to a second value of the electrical characteristic of the thermoelectric device and/or in response to temperature feedback data generated by the temperature feedback sensor.

7. The temperature control system of claim 1, wherein said controller is configured to cyclically activate the thermoelectric device.

8. The temperature control system of claim 1, wherein said controller is configured to provide thermal pulses to the temperature controlled medium.

9. The temperature control system of claim 1, wherein said controller is configured to maintain a stable temperature of the temperature controlled medium.

10. The temperature control system of claim 1, wherein said controller is configured to cyclically alter the temperature profile of the temperature controlled medium.

11. The temperature control system of claim 1, wherein said controller is configured to provide a temperature ramp for the temperature controlled medium.

12. The temperature control system of claim 1, wherein said controller is configured to cool the tissue adjacent to said temperature controlled medium between about 1 and about 20 degrees Centigrade.

13. The temperature control system of claim 1, wherein said controller is configured to heat the tissue adjacent to said temperature controlled medium between about 1 and about 20 degrees Centigrade.

14. The temperature control system of claim 1, wherein said medical instrument is configured to be insertable into an ear canal of a subject.

15. The temperature control system of claim 1, wherein said medical instrument is a vestibular system stimulator.

16. The temperature control system of claim 15, wherein said vestibular system stimulator is configured to deliver caloric vestibular stimulation.

17. The temperature control system of claim 1, wherein said medical instrument is a nerve stimulation probe.

18. The temperature control system of claim 17, wherein said nerve stimulation probe is a vagal nerve stimulation probe.

19. A method of treating a subject, comprising:
positioning the temperature controlled medium of claim 1 in an ear canal of a subject; and
activating the thermoelectric device of claim 1 sufficient to treat the subject.

20. A method of delivering caloric vestibular stimulation to a subject, comprising:
positioning the temperature controlled medium of claim 1 in an ear canal of a subject; and
activating the thermoelectric device of claim 1 to deliver caloric vestibular stimulation to the subject.

21. A method of stimulating a nerve in a subject in need thereof, comprising:
positioning the temperature controlled medium of claim 1 in an ear canal of a subject; and
activating the thermoelectric device of claim 1 to stimulate a nerve.

22. A method of reducing pain in a subject, comprising:
positioning the temperature controlled medium of claim 1 in an ear canal of a subject; and
activating the thermoelectric device of claim 1 to treat migraine headache pain.

23. The temperature control system of claim 1, wherein the controller is configured to provide thermal pulses from about one-half second to about two minutes in duration.

24. A temperature control system comprising:
a thermoelectric device;
a controller electrically coupled to the thermoelectric device;
a heat transfer structure thermally coupled to a first side of the thermoelectric device; and
a temperature controlled medium thermally coupled to a second side of the thermoelectric device so that the thermoelectric device is thermally coupled between the heat transfer structure and the temperature controlled medium, wherein said temperature controlled medium comprises a medical instrument configured to contact living tissue,
wherein said controller is configured to cyclically activate the thermoelectric device and a cycle includes ramping to a first desired temperature or heat flux, maintaining the first desired temperature or heat flux for a period of time, and then ramping to a second desired temperature or heat flux and holding the second desired temperature or heat flux for a second period of time,
wherein the temperature control system further comprises a temperature feedback sensor, wherein said controller is configured to generate a first electrical control signal to activate said thermoelectric device and said first electrical control signal is generated in response to a first value of the electrical characteristic of the thermoelectric device, wherein the electrical characteristic of the thermoelectric device comprises an electrical characteristic of the thermoelectric device indicating one of a temperature gradient across the thermoelectric device and a temperature of the temperature controlled medium.

25. The temperature control system of claim 24, wherein said controller is configured to maintain a stable temperature of the temperature controlled medium.

26. The temperature control system of claim 24, wherein said controller is configured to cyclically alter the temperature profile of the temperature controlled medium.

27. The temperature control system of claim 24, wherein said controller is configured to provide a temperature ramp for the temperature controlled medium.

28. The temperature control system of claim 24, wherein said controller is configured to cool the tissue adjacent to said temperature controlled medium between about 1 and about 20 degrees Centigrade.

29. The temperature control system of claim 24, wherein said controller is configured to heat the tissue adjacent to said temperature controlled medium between about 1 and about 20 degrees Centigrade.

30. The temperature control system of claim 24, wherein said medical instrument is configured to be insertable into an ear canal of a subject.

31. The temperature control system of claim 24, wherein said medical instrument is a vestibular system stimulator.

32. The temperature control system of claim 31, wherein said vestibular system stimulator is configured to deliver caloric vestibular stimulation.

33. The temperature control system of claim 24, wherein said medical instrument is a nerve stimulation probe.

34. The temperature control system of claim 33, wherein said nerve stimulation probe is a vagal nerve stimulation probe.

35. A method of treating a subject, comprising:
positioning the temperature controlled medium of claim 24 in an ear canal of a subject; and
activating the thermoelectric device of claim 24 sufficient to treat the subject.

36. A method of delivering caloric vestibular stimulation to a subject, comprising:
positioning the temperature controlled medium of claim 24 in an ear canal of a subject; and
activating the thermoelectric device of claim 24 to deliver caloric vestibular stimulation to the subject.

37. A method of stimulating a nerve in a subject in need thereof, comprising:
positioning the temperature controlled medium of claim 24 in an ear canal of a subject; and
activating the thermoelectric device of claim 24 to stimulate the nerve.

38. A method of reducing pain in a subject, comprising:
positioning the temperature controlled medium of claim 24 in an ear canal of a subject; and
activating the thermoelectric device of claim 24 to treat migraine headache pain.

39. The temperature control system of claim 24, wherein the controller is configured to cyclically activate the thermoelectric device with each cycle lasting from about one minute to about ten minutes in duration.

40. A temperature control system comprising:
a thermoelectric device;
a controller electrically coupled to the thermoelectric device;
a heat transfer structure thermally coupled to a first side of the thermoelectric device; and
a temperature controlled medium thermally coupled to a second side of the thermoelectric device so that the thermoelectric device is thermally coupled between the heat transfer structure and the temperature controlled medium, wherein said temperature controlled medium comprises a medical instrument configured to contact living tissue,
wherein said controller is configured to cyclically alter the temperature profile of the temperature controlled medium, and a temperature profile cycle includes ramping to a first desired temperature or heat flux, maintaining the first desired temperature or heat flux for a period of time, and then ramping to a second desired temperature or heat flux and holding the second desired temperature or heat flux for a second period of time, wherein the temperature control system further comprises a temperature feedback sensor, wherein said controller is configured to generate a first electrical control signal to activate said thermoelectric device and said first electrical control signal is generated in response to a first value of the electrical characteristic of the thermoelectric device, wherein the electrical characteristic of the thermoelectric device comprises an electrical characteristic of the thermoelectric device indicating one of a temperature gradient across the thermoelectric device and a temperature of the temperature controlled medium.

41. The temperature control system of claim 40, wherein said controller is configured to maintain a stable temperature of the temperature controlled medium.

42. The temperature control system of claim 41, wherein said medical instrument is a nerve stimulation probe.

43. The temperature control system of claim 42, wherein said nerve stimulation probe is a vagal nerve stimulation probe.

44. The temperature control system of claim 40, wherein said controller is configured to cyclically alter the temperature profile of the temperature controlled medium.

45. The temperature control system of claim 40, wherein said controller is configured to provide a temperature ramp for the temperature controlled medium.

46. The temperature control system of claim 40, wherein said controller is configured to cool the tissue adjacent to said temperature controlled medium between about 1 and about 20 degrees Centigrade.

47. The temperature control system of claim 40, wherein said controller is configured to heat the tissue adjacent to said temperature controlled medium between about 1 and about 20 degrees Centigrade.

48. The temperature control system of claim 40, wherein said medical instrument is configured to be insertable into an ear canal of a subject.

49. The temperature control system of claim 40, wherein said medical instrument is a vestibular system stimulator.

50. The temperature control system of claim 49, wherein said vestibular system stimulator is configured to deliver caloric vestibular stimulation.

51. A method of treating a subject, comprising:
   positioning the temperature controlled medium of claim 40 in the ear canal of a subject; and
   activating the thermoelectric device of claim 40 sufficient to treat the subject.

52. A method of delivering caloric vestibular stimulation to a subject, comprising:
   positioning the temperature controlled medium of claim 40 in the ear canal of a subject; and
   activating the thermoelectric device of claim 40 to deliver caloric vestibular stimulation to the subject.

53. A method of stimulating a nerve in a subject in need thereof, comprising:
   positioning the temperature controlled medium of claim 40 in an ear canal of a subject; and
   activating the thermoelectric device of claim 40 to stimulate the nerve.

54. A method of reducing pain in a subject, comprising:
   positioning the temperature controlled medium of claim 40 in the ear canal of a subject; and
   activating the thermoelectric device of claim 40 to treat migraine headache pain.

55. The temperature control system of claim 40, wherein the controller is configured to cyclically alter the temperature profile of the temperature controlled medium with each cycle lasting from about one minute to about ten minutes in duration.

* * * * *

UNITED STATES PATENT AND TRADEMARK OFFICE
CERTIFICATE OF CORRECTION

PATENT NO. : 10,390,991 B2
APPLICATION NO. : 13/584853
DATED : August 27, 2019
INVENTOR(S) : Rogers et al.

It is certified that error appears in the above-identified patent and that said Letters Patent is hereby corrected as shown below:

In the Specification

Column 1, Line 44: Please correct "Te$_{3\text{-}n}$" to read -- Te$_{3\text{-}x}$ --

Column 1, Line 57: Please correct "p" to read -- $\rho$ --

Column 1, Line 57: Please correct "a" to read -- $\alpha$ --

Signed and Sealed this
Fourth Day of February, 2020

Andrei Iancu
*Director of the United States Patent and Trademark Office*